United States Patent [19]
Frigerio et al.

[11] Patent Number: 5,444,082
[45] Date of Patent: Aug. 22, 1995

[54] 3,9-DISUBSTITUTED-SPIRO(5.5)UNDECANES ACTIVE ON THE CARDIOVASCULAR SYSTEM, PROCESS FOR THEIR PREPARATION AND PHARMACEUTICAL COMPOSITION CONTAINING SAME

[75] Inventors: Marco Frigerio, Milan; Patrizia Ferrari, Varese; Piero Melloni, Bresso; Giuliana Salani, Villongo, all of Italy

[73] Assignee: Sigma-Tau Industrie Farmaceutiche Riunite S.p.A., Rome, Italy

[21] Appl. No.: 82,372

[22] Filed: Jun. 28, 1993

[30] Foreign Application Priority Data

Jul. 8, 1992 [DE] Germany .................. 42 22 459.4

[51] Int. Cl.$^6$ .................. A61K 31/415; C07D 405/08; C07D 405/12
[52] U.S. Cl. .................. 514/409; 514/255; 514/278; 514/397; 514/399; 514/401; 514/438; 514/444; 514/462; 514/632; 514/634; 546/15; 548/300.7; 548/407; 549/74; 549/75; 549/330; 564/227
[58] Field of Search .............. 544/6, 20, 230; 546/15; 548/300.7, 407; 549/74, 75, 330; 564/227; 514/255, 278, 397, 399, 401, 409, 438, 444, 462, 632, 634

[56] References Cited

U.S. PATENT DOCUMENTS

| | | | |
|---|---|---|---|
| 3,256,277 | 6/1966 | Rice | 546/15 |
| 3,825,546 | 7/1974 | Rice | 546/15 |
| 4,098,823 | 7/1978 | Arndt | 424/305 |
| 4,737,503 | 4/1988 | Sakamoto | 514/279 |
| 4,963,557 | 10/1990 | Dadger | 546/16 |
| 5,234,922 | 8/1993 | Welsh | 514/223.2 |

OTHER PUBLICATIONS

Hamer et al "Drugs for heart disease" Chapman & Hall Publisher, pp. 383-385 (1979).
Berger "Medicinal Chemistry" Interscience Publisher, pp. 565-571, 579-581, 600-601 (1960).
Brown, L. & Erdmann, E., "Comparison of the Affinity of Human, Beef and Cat Heart $(Na^+ + K^+)$-ATPase for for Different Digitalis Derivatives", Arzneim-Forsch., 1984, 34 (II), 1314.
Jorgensen, Peter Leth, "Purification adn Characterization of $(Na^+ - K^+)$-ATPase III. Purification from the Outer Medulla of Mammalian Kidney After Selective Removal of Membrane Components by Sodium Dodecylsulpate", Biochimica et Biophysica Acta, (1974), pp. 36–51.
Noel, F, and Godfraind, T., "Heterogeneity of Ouabain Specific Binding Sites and $(Na + + K - -ATPase$ Inhibition in Microsomes From Rat Heart", Laboratoire de Pharmacodynamie Generale et de Pharmacologie, Universite Catholique de Louvain., Bruxelles, Belgium, Accepted Jul. 12, 1983.

*Primary Examiner*—Ceila Chang
*Attorney, Agent, or Firm*—Oblon, Spivak, McClelland, Maier & Neustadt

[57] ABSTRACT

3,9-disubstituted-spiro[5.5]undecanes and

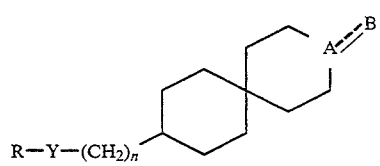

wherein, R, Y, A, B and n are defined in the specification, pharmaceutical compositions containing same for the treatment of cardiovascular disorders, such as heart failure and hypertension, are disclosed.

6 Claims, No Drawings

3,9-DISUBSTITUTED-SPIRO(5.5)UNDECANES ACTIVE ON THE CARDIOVASCULAR SYSTEM, PROCESS FOR THEIR PREPARATION AND PHARMACEUTICAL COMPOSITION CONTAINING SAME

The present invention relates to new 3,9-disubstituted-spiro[5.5]-undecanes active on the cardiovascular system, to a process for their preparation and to pharmaceutical compositions containing same for the treatment of cardiovascular disorders, such as heart failure and hypertension. The compounds of the invention have the following general formula (I):

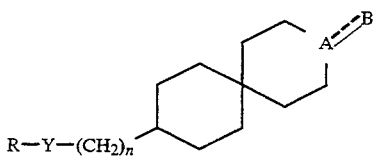

wherein:
R represents:
  hydrogen or
  a $C_2$–$C_6$ alkyl or $C_2$–$C_6$ alkenyl group unsubstituted or substituted independently by a quaternary ammonium group or one or more hydroxy, $C_1$–$C_6$ alkoxy, carboxy, $NR_4R^5$, NHC(NH)NHR$^6$ or C(NH)NR$^7R^8$ groups, wherein
    $R^4$ and $R^5$, which may be the same or different, are H, $C_1$–$C_6$ lower alkyl group, benzyl or phenyl or $R^4$ and $R^5$, taken together with the nitrogen atom, form an unsubstituted or substituted saturated or unsaturated mono-heterocyclic 5- or 6-membered ring optionally containing another heteroatom chosen from oxygen, sulphur or nitrogen,
    $R^6$, $R^7$ and $R^8$, which are the same or different, may be H or $C_1$–$C_4$ lower alkyl;
n is an integer from 0 to 4; and
Y is oxygen or sulphur;
the symbol --- means single or double bond with the proviso that
  (i) when --- is a single bond
    A represents a C—H or C—OR$^1$ group wherein R$^1$ is H or CH$_3$ and
    B represents:
      a $C_1$–$C_6$ lower alkyl or $C_2$–$C_6$ alkenyl chain substituded by:
        (a) hydroxy, amino, oxo, =N—NR$^2$—C(=Z)NHR$^3$ groups wherein R$^2$ and R$^3$, which may be the same or different, are H, $C_1$–$C_6$ lower alkyl, benzyl or phenyl or R$^2$ and R$^3$, taken together with the nitrogen atoms, form an unsubstituted or substituted saturated or unsaturated mono-heterocyclic 5-or 6-menbered ring, and Z is oxygen, sulphur or NR$^9$ wherein R$^9$ is H, $C_1$–$C_4$ lower alkyl group, CN or taken together with R$^2$ or R$^3$ form an unsubstituted or substituted mono-heterocyclic 5- or 6-membered ring;
        (b) a saturated or unsaturated mono-heterocyclic 5- or 6-membered ring, containing one or more heteroatoms chosen from the group of O, S or N, unsubstituted or substituted by one or more hydroxy, oxo, amino or $C_1$–$C_6$ lower alkyl group; and
  (ii) when --- is a double bond
    A represents a carbon atom C and
    B represents:
      a =N—NR$^2$—C(=Z)NHR$^3$ group, wherein R$^2$, R3 and Z have the above-identified meanings.

Also the pharmaceutically acceptable salts as well as the optical antipodes, i.e. the enantiomers, the racemic mixture of the optical antipodes, or other mixtures thereof, the geometric isomers and their mixtures, the diastereoisomers and mixtures of diastereoisomers of compounds of formula (I) are included in the scope of the invention.

Also encopassed within the scope of the invention are the metabolites and the metabolic precursors of compounds of formula (I).

Pharmaceutically acceptable salts of (I) are salts which retain the biologically activity of the base or the acid and are derived from such known pharmaceutically acceptable acids such as e.g. hydrochloric, sulphuric, phosphoric, malic, tartaric, maleic, citric, methanesulphonic or benzoic acids or from such known bases as sodium, potassium or calcium hydroxides.

The alkyl, alkenyl and alkynyl groups may be branched or straight chain groups.

The $C_1$–$C_6$ alkyl group is preferably a $C_1$–$C_4$ alkyl group, e.g. methyl, ethyl, propyl, isopropyl, butyl, sec-butyl or tert-butyl.

The $C_2$–$C_6$ alkenyl group is preferably a $C_2$–$C_4$ alkenyl group.

The $C_2$–$C_6$ alkynyl group is preferably a $C_2$–$C_4$ alkynyl group.

The quaternary ammonium group is preferably a $C_1$–$C_4$ trialkylammonium or a N-methylpyrrolidinium or a N-methylpiperidinium group.

The =N—NR$^2$—C(=Z)NHR$^3$ group is preferably guanidinoimino, ureidoimino, thioureidoimino, N-methylguanidinoimino (i.e: R$^3$= methyl), N,N'-dimethylguanidinoimino (i.e; R$^2$ and R$^3$=methyl), (2-imidazolin-2-yl)hydrazono or 2-(2-imidazolyl)hydrazono.

The NR$^4R^5$ group is preferably amino, methylamino, ethylamino, propylamino, isopropylamino, allylamino, propargylamino, dimethylamino, pyrrolidinyl, morpholino, piperazinyl, 4-methylpiperazinyl, 4-ethylpiperazinyl, 4-phenylpiperazinyl, 1-imidazolyl, guanidino, 2-aminoethylamino, 3-aminopropylamino, 2-(1-pyrrolidinyl)ethylamino, 3-(1-pyrrolidinyl)propylamino, 3-amino-2-hydroxypropylamino, 3-(1-pyrrolidinyl)-2-hydroxypropylamino or 2,3-diaminopropylamino.

The $C_1$–$C_6$ alkoxy group is preferably methoxy, ethoxy, isopropoxy, n-butoxy or tert-butoxy. The saturated or unsaturated mono-heterocyclic ring is preferably oxyranyl, 2-aziridinyl, 2-furyl, 2-thienyl, 2-imidazolyl, 2-pirrolyl, 2-tetrahydrofuryl, 3-furyl, 3-thienyl, 4-imidazolyl, 3-pirrolyl, 3-tetrahydrofuryl, 2-oxo-(5H)-3-furyl, 2-oxo-(5H)-4-furyl, 2-thiazolyl, 2-pyridinyl, 3-pyridinyl, 4-pyridinyl, 2-pyrimidyl, 4-pyrimidyl, 5-pyrimidyl, 2-pyridinyl-N-oxide, 3-pyridinyl-N-oxide, 2-oxo-(1H)-4-pyridinyl, 2-oxo-(1H)-5-pyridinyl or 2-oxo-(2H)-5-pyranyl.

Specific examples of preferred compounds (I) of the invention are:
(EZ)-9-(2-(N-pyrrolidinyl)ethoxy)-3-(2-(3-furyl)vinyl)-spiro[5.5]undecane
9-(2-(N-pyrrolidinyl)ethoxy)-3-(2-(3-furyl)ethyl)-spiro[5.5]undecane 9-(2-(N-pyrrolidinyl)ethoxy)-3-(2-(3-thienyl)ethyl)-spiro[5.5]undecane
9-(2-(N-pyrrolidinyl)ethoxy)-3-(2-(2-oxo-[5H]-3-furyl)ethyl)-spiro[5.5]undecane
9-(2-(N-pyrrolidinyl)ethoxy)-3-(2-(2-oxo-[5H]-4-furyl)ethyl)-spiro[5.5]undecane
9-(2-(N-pyrrolidinyl)ethoxy)-3-(2-(3-pyridyl)ethyl)-spiro[5.5]undecane
9-(2-(N-pyrrolidinyl)ethoxy)-3-(2-(3-pyridyl-N-oxide)ethyl)-spiro[5.5]undecane
9-(2-(N-pyrrolidinyl)ethoxy)methyl-3-(3-furyl)methyl-spiro[5.5]undecane
9-(2-(N-pyrrolidinyl)ethoxy)methyl-3-(3-pyridyl)methyl-spiro[5.5]undecane
9-(2-(N-pyrrolidinyl)ethoxy)methyl-3-(2-thiazolyl)methyl-spiro[5.5]undecane
9-(2-(N-pyrrolidinyl)ethoxy)methyl-3-(2-oxo-(2H)-5-pyranyl)methyl-spiro[5.5]undecane
9-(3-(N-pyrrolidinyl)propoxy)-3-(2-(3-furyl)ethyl)-spiro[5.5]undecane
9-(2-(4-methylpiperazin-1-yl)ethoxy)-3-(2-(3-furyl)ethyl)spiro[5.5]undecane
9-(2-aminoethoxy)-3-(2-(3-furyl)ethyl)-spiro[5.5]undecane
9-(3-aminopropoxy)-3-(2-(3-furyl)ethyl)-spiro[5.5]undecane
9-(3-aminopropoxy)-3-(2-(3-thienyl)ethyl)-spiro[5.5]undecane
9-(3-(N-pyrrolidinyl)propoxy)methyl-3-(3-furyl)methyl-spiro[5.5]undecane
(EZ)-9-(2-(N-pyrrolidinyl)ethoxy)methyl-3-(3-furyl)methyliden-spiro[5.5]undecane
(EZ)-9-(2-(N-pyrrolidinyl)ethoxy)methyl-3-(2-(2-oxo-[5H]-4-furyl))methyliden-spiro[5.5]undecane
9-(2-aminoethoxy)methyl-3-(3-furyl)methyl-spiro[5.5]undecane
9-(3-aminopropoxy)methyl-3-(3-furyl)methylspiro[5.5]undecane
9-(2-amino-3-hydroxypropoxy)-3-(2-(3-furyl)ethyl)-spiro[5.5]undecane
9-(3-amino-2-hydroxypropoxy)-3-(2-(3-furyl)ethyl)-spiro[5.5]undecane
9-(3-methoxy-2-hydroxypropoxy)-3-(2-(3-furyl)ethyl)-spiro[5.5]undecane
9-(2,3-dihydroxypropoxy)-3-(2-(3-furyl)ethyl)-spiro[5.5]undecane
9-(2-(N-pyrrolidinyl)ethoxy)-3-(2-(3-furyl)ethyl)-3-hydroxy-spiro[5.5]undecane
9-(2-(N-pyrrolidinyl)ethoxy)-3-(2-(3-furyl)ethyl)-3-amino-spiro[5.5]undecane
9-(2-aminoethylthio)-3-(2-(3-thienyl)ethyl)-spiro[5.5]undecane
9-(2-aminoethylthio)methyl-3-(3-furyl)methyl-spiro[5.5]undecane
9-(2-aminoethylthio)methyl-3-(3-thienyl)methyl-spiro[5.5]undecane
9-(2-(N-pyrrolidinyl)ethylthio)-3-(2-(3-furyl)ethyl)-3-hydroxy-spiro[5.5]undecane
9-(2-(N-pyrrolidinyl)ethoxy)methyl-3-(3-furyl)methyl-3-hydroxy-spiro[5.5]undecane
9-(2-(N-pyrrolidinyl)ethylthio)methyl-3-(3-thienyl)methyl-3-hydroxy-spiro[5.5]undecane
9-(2-(N-pyrrolidinyl)ethoxy)-3-guanidinoimino-spiro[5.5]undecane
9-(2-(N-pyrrolidinyl)ethoxy)-3-guanidinoiminomethyl-spiro[5.5]undecane
9-(2-(N-pyrrolidinyl)ethoxy)methyl-3-guanidinoiminomethyl-spiro[5.5]undecane
9-(2-(N-pyrrolidinyl)ethoxy)-3- [2-(imidazolin-2-yl)hydrazono]-methyl-spiro[5.5]undecane
9-(2-(N-pyrrolidinyl)ethoxy)-3-[2-(2-imidazolyl)hydrazono]-methyl-spiro[5.5]undecane
(EZ)-9-hydroxy-3-(2-(3-furyl)vinyl)-spiro[5.5]undecane
(EZ)-9-hydroxy-3-(2-(3-thienyl)vinyl)-spiro[5.5]undecane
(EZ)-9-hydroxy-3-(2-(2-oxo-[5H]-3-furyl)vinyl)-spiro[5.5]undecane
(EZ)-9-hydroxy-3-(2-(2-oxo-[5H]-4-furyl)vinyl)-spiro[5.5]undecane
(E)-9-hydroxy-3-(2-(3-pyridyl)vinyl)-spiro[5.5]undecane
(Z)-9-hydroxy-3-(2-(3-pyridyl)vinyl)-spiro[5.5]undecane
(EZ)-9-hydroxymethyl-3-(3-furyl)methyliden-spiro[5.5]undecane
(EZ)-9-hydroxymethyl-3-((2-oxo-[5H]-3-furyl))methylidenspiro[5.5]undecane
(EZ)-9-hydroxymethyl-3-((2-oxo-[5H]-4-furyl))methylidenspiro[5.5]undecane
9-hydroxy-3-(2-(3-furyl)ethyl)-spiro[5.5]undecane
9-hydroxy-3-(2-(3-pyridyl)ethyl)-spiro[5.5]undecane
9-hydroxy-3-(2-(3-pyridyl-N-oxide)ethyl)-spiro[5.5]undecane
9-hydroxymethyl-3-(3-furyl)methyl-spiro[5.5]undecane
9-hydroxymethyl-3-(3-pyridyl)methyl-spiro[5.5]undecane
9-hydroxymethyl-3-(3-furyl)methyl-3-hydroxyspiro[5.5]undecane
9-hydroxy-3-guanidinoimino-spiro[5.5]undecane
9-hydroxy-3-[2-(2-imidazolin-2-yl)hydrazono]-spiro[5.5]undecane
9-hydroxy-3-[2-(2-imidazolyl)hydrazono]-spiro[5.5]undecane
9-hydroxy-3-guanidinoiminomethyl-spiro[5.5]undecane
9-hydroxy-3-ureidoiminomethyl-spiro[5.5]undecane
9-hydroxy-3-[2-(2-imidazolin-2-yl)hydrazono]methyl-spiro[5.5]undecane
9-hydroxy-3-[2-(2-imidazolyl)hydrazono]methyl-spiro[5.5]undecane
9-hydroxy-3-thioureidoiminoethyl-spiro[5.5]undecane
9-hydroxy-3-(2-guanidinoimino)ethyl-spiro[5.5]undecane
9-hydroxy-3-(1-guanidinoimino)ethyl-spiro[5.5]undecane
9-hydroxy-3-(3-guanidinoimino)propyl-spiro[5.5]undecane
9-hydroxymethyl-3-guanidinoimino-spiro[5.5]undecane
9-hydroxymethyl-3-[2-(2-imidazolin-2-yl)hydrazono]-spiro[5.5]undecane
9-hydroxymethyl-3-[2-(2-imidazolyl)hydrazono]-spiro[5.5]undecane
9-hydroxymethyl-3-guanidinoiminomethyl-spiro[5.5]undecane
9-hydroxy-3-hydroxy-3-guanidinoiminomethyl-spiro[5.5]undecane
9-hydroxymethyl-3-[2-(imidazolin-2-yl)hydrazono]-methyl-spiro[5.5]undecane
9-hydroxymethyl-3-[2-(2-imidazolyl)hydrazono]methyl-spiro[5.5]undecane
9-hydroxymethyl-3-hydroxy-3-guanidinoiminomethyl-spiro[5.5]undecane The parent compound spiro[5.5]undecane, as well as simple alkyl derivatives thereof, have been the object of theoretical studies in stereochemistry (Dodziuk H., *J. Chem. Soc., Perkin. Trans.*, 1986, 2, 249; Tavernier D., *Bull. Soc. Chim. Belg.*, 1987, 96, 253), molecular mechanics (Ioffe A. et. al., *Izv. Akad. Nauk. SSSR, Ser. Khim.*, 1987, 801: C. A. 108, 111418k), and thermodynamics (Flizar S. & Cantara J. L., *Can. J. Chem.*, 1981, 59, 1381; Gund P. & Gund T. M., *J. Am. Chem. Soc.*, 1981, 103, 4458–65.).

Some halogenated marine natural diterpenes, having the spiro[5.5]undecane skeleton, have been isolated from extracts of sea algae or sea hare (Pargeurol: Schmitz F. J. et al., *J. Am. Chem. Soc.*, 1982, 104, 6415; Majuscolone: Suzukin M. et al., *Bull. Chem. Soc. Jpn.*, 1987, 60, 3795; Chamigrane: Brennan M. R. et al., *Phytochemistry*, 1987, 26, 1053). Chamigrane has been claimed to posses antiviral activity (WO 86/03, 793, 03 Jul. 1986).

Some polyalkyl derivatives of spiro[5.5]undecane have been claimed to be useful in augmenting and enhancing the aroma of perfume composition (U.S. Pat. No. 4,622,172, 11 Nov. 1986). Different spirocycloalkanes, spiro[5.5]undecane as well as dispiro[3.1.3.1]decane, have been reported to posses liquid crystals properties (Karamysheva L. A. et al., *Mol. Cryst. Liq. Cryst.*, 1983, 143, 169; Chan L. K. M. et al., *Mol. Cryst. Liq. Cryst.*, 1987, 147, 113; WO 88/09, 322, 01 Dec. 1988).

Structural as well as pharmacobiological differences between the compounds of the present invention and the already known derivatives of spiro[5.5]undecane are evident.

The invention furthermore provides a process for the preparation of compounds of general formula (I), which comprises the condensation of compounds of general formula (II):

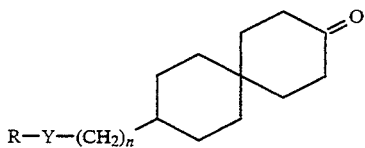

II wherein R, Y and n are as above defined, with a nucleophile chosen in the group of $NH_2-NR^2-C(=Z)NHR^3$, wherein $R^2$, $R^3$ and Z are as above defined, and $B^1-M$ wherein $B^1$ represents:

- a saturated or unsaturated 5- or 6-membered monoheterocyclic ring, containing one or more heteroatoms chosen from the group of O, S or N, unsubstituted or substituted by one or more hydroxy, oxo, amino or $C_1-C_6$ lower alkyl group;
- a $C_1-C_6$ lower alkyl, $C_2-C_6$ alkenyl or $C_2-C_6$ alkynyl group substituted by:
  hydroxy, amino, oxo groups
    a saturated or unsaturated 5- or 6-membered monoheterocyclic ring, containing one or more heteroatoms chosen from the group of O, S or N, unsubstituted or substituted by one or more hydroxy, oxo, amino or $C_1-C_6$ lower alkyl group, and M represents a metal chosen in the group of Mg, Li, Cu, Zn, Sm and Ce or a triphenylphosphonium salt $[(C_6H_5)P^+X^-]$ or a phosphonate group $[P(O)(OR^{10})2]$ wherein $X-$ is chloride or bromide ion and $R^{10}$ is methyl or ethyl, the free hydroxy, amino, carboxy and oxo groups if any present in R and/or $B^1$ being protected with methods well known to those skilled in the art, to give after removal of protective groups if any present in R and/or $B^1$, a compound of general formula (I)which may be converted into another compound of general formula (I) and/or, if desired, subjected to salification and/or isomer separation.

The reaction between a compound of general formula (II) and a nucleophile of general $NH_2-NR^2-C(=Z)NHR^3$ is performed in a solvent such as tetrahydrofuran, dioxane, dimethylformamide, dimethyl-sulfoxide, benzene, toluene, dichloromethane, methanol, ethanol, water or their mixtures, at a temperature ranging from 0° C. to the reflux temperature of the reaction mixture. The reaction may be conducted in the presence of a base, such as sodium or potassium hydroxide, sodium or potassium carbonate, or in presence of an acid such as, hydrochloric acid, hydrobromic acid or acetic acid, these operating conditions depending mainly on the nature of other functional group in R or B. The reaction time varies from a few minutes to several hours.

The condensation reactions between a compound of general formula (II) and a compound of general formula $B^1-M$ are carried out either at the same conditions as those of a metallorganic reaction (when M represents a metal) or at the conditions of a Wittig reaction (when M represents a phosponium salt or a phosponate).

The metallorganic condensations are best carried out in a solvent, such as diethylether, tetrahydrofuran, dioxane, benzene or their mixtures, at a temperature ranging from $-78°$ C. to the reflux temperature of the reaction mixture; the reaction time varies from a few minutes to several hours. The preferred conditions depend mainly on the nature of the metal, so that when M is lithium or cerium the temperature tipically ranges from $-78°$ to 0° C., while when M is magnesium or samarium it ranges from o 15° to 50° C.

The Wittig condensation with a phosphonium salt or a phosphonate is best carried out in a solvent, such as tetrahydrofuran, dioxane, dimethylformamide, dimethylsulfoxide, benzene, toluene, dichloromethane, methanol, ethanol or their mixtures, in the presence of a strong base such as, for example sodium or potassium hydride, sodium or potassium ethoxide sodium or potassium methoxide, potassium tert-butoxide, butyl-lithium, sodium methylsulfinylmethide, at a temperature ranging from $-78°$ C. to the reflux temperature of the reaction mixture; the reaction time varies from few minutes to several hours.

The triphenylphosphonium salts or phosphonates are converted into an ylide under the above listed basic conditions; the ylide may be prepared both in situ, in the presence of the compound of general formula (II), or even in a separated reaction vessel depending on the stability of the ylide.

The conversion of one compound of general formula (I) into another compound of general formula (I) may involve e.g. the hydrogenation of a double bond by standard procedures (e.g.: hydrogenation over Pd, Pt or Ni) or the reduction of a keto group to an alcohol, the alkylation of an alcohol to ether, or the alkylation of a mercaptane to a thioether, as well as the reaction of a keto group optionally present in $B^1$ with compounds of general formula $NH_2-NR^2-C(=Z)NHR^3$, or the oxidation of a furan ring into a 2-oxo-5H-furan group, all said transformations being well established procedure in organic chemistry, (see for example: J. March "*Advanced Organic Chemistry*", J. Wiley & Sons, 1985, Wiesner K. et al., *Helv. Chim. Acta*, 1984, 67, 1128). Compounds of general formula (II):

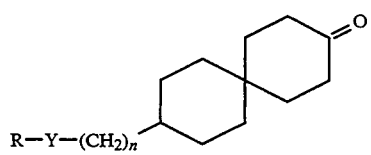

wherein R is different from H and n is different from zero, are prepared from compound IIa:

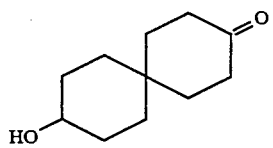

which, if desired, can be transformed into another compound of general formula (II) by converting, for example, the hydroxy group into a mercapto or homologating the hydroxy group into an hydroxymethyl group, hydroxyethyl, hydroxypropyl, hydroxybutyl, homologating the hydroxy to mercaptomethyl, mercaptoethyl mercaptopropyl, mercaptobutyl and/or converting the alcoholic function into an ether, and/or converting a mercaptane into a thioether by standard methods well known to those skilled in the art (see for example: J. March "Advanced Organic Chemistry", J. Wiley & Sons, 1985).

Compound IIa is prepared from known 3,9-dioxo-spiro[5.5]undecane (III) (Rice L. M. et al., J. Org. Chem., 1967, 32, 1966):

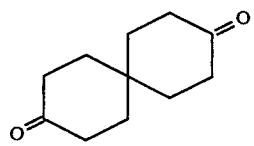

by reduction, with less than an equivalent of sodium borohydride of only one of the two equivalent keto groups to give 9-hydroxy-3-oxo-spiro[5.5]undecane (II-a).

The compounds of general formula (I) prepared according to the invention and their pharmaceutically acceptable salts are useful agents for the treatment of cardiovascular disorders such as heart failure and hypertension.

The compounds of general formula (I) prepared according to the invention and their pharmaceutically acceptable salts have highly reduced toxicity compared to known positive inotropic agents such as ouabain and digitoxin.

Moreover said compounds (I) show good affinity for the receptor site of the $Na^+,K^+$-ATPase and behave as partial agonists on the enzymatic activity of the $Na^+,K^+$-ATPase.

To test the affinity for the receptor site of the $Na^+,K^+$-ATPase and the agonist or antagonist activity on the enzyme, the following tests are used: a) displacement of the specific 3-Houabain binding from the $Na^+,K^+$-ATPase receptor purified according to Jorgensen (Jorgensen P., BBA, 1974,356, 36) and Erdmann (L. Brown and E. Erdmann., Arzneim. Forsh., 1984, 34 (II), 1314); b) inhibition of the activity of the purified $Na^+,K^+$-ATPase measured as % of hydrolysis of $^{32}P$-ATP in presence and in absence of the tested compound (F. Noel and Godfraind., Biochem. Pharmacol., 1984, 33, 47). The activity of some compounds of general formula (I) on the two tests are shown in the following table:

TABLE 1

|  | Binding $^3$H-Ouab. Displacement -log. $IC_{50}$ | Inhibitory Activity -log $IC_{50}$ |
|---|---|---|
| Comp. I-g | 4.9 | 4.8 |
| Comp. I-j | 5.1 | 4.3 |
| Comp. I-m | 4.5 | 4.3 |
| Comp. I-r | 4.5 | 4.9 |
| Comp. I-ab | 4.8 | 4.8 |
| Comp. I-a | 4.1 | 4.6 |
| Comp. I-h | 4.6 | 4.0 |
| Comp. 1-i | 4.0 | 4.0 |
| Comp. I-t | 4.0 | 4.3 |
| Comp. I-u | 4.3 | 4.3 |
| Comp. I-x | 4.0 | 4.0 |
| Comp. I-ay | 4.6 | 4.0 |
| Comp. I-az | 4.8 | 4.2 |
| Comp. I-bf | 4.4 | 4.0 |
| Comp. 1-be | 5.0 | 4.8 |
| Comp. I-bh | 4.2 | 4.0 |
| Comp. 1-bg | 4.0 | 4.0 |

To obtain the desired therapeutic effect, the compound of the invention of general formula (I) may be administered to the patient in different way, in pharmaceutical preparation by oral, parenteral, nasal or rectal route. A pharmaceutical composition suitable for this purpose can be prepared according well known techniques.

The following examples illustrate the invention without limiting it.

EXAMPLE 1

(EZ)-9-(2(N-Pyrrolidinyl)ethoxy)-3-(2-(3-furyl)vinyl)-spiro[5.5]undecane I-a

Sodium hydride (1.87 g, 60% dispersion in oil) was added to a solution of 2.59 g of (EZ)-9-hydroxy-3-(2-(3-furyl)vinyl)-spiro[5.5]undecane (I-ag, Ex. 31) and 3.77 g of N-(2-chloroethyl)-pyrrolidine in 15 ml of anhydrous tetrahydrofuran, under argon atmosphere at room temperature. The mixture was refluxed for 2.5 hrs in a Dean-Stark apparatus, collecting part of the distilled solvent to the point of having a pasty stirrable residue. The mixture was cooled to room temperature, brine and ethyl acetate were added, the organic layer separated and extracted several times with HCl 1N.

The collected aqueous phase was neutralised with potassium hydroxide 4N and extracted with ethyl acetate to give, after workup, 3.59 g of a brown-yellowish oil which was purified by column chromatography ($SiO_2$; chloroform/methanol 90/10) to give 2.94 g of (EZ)-9-(2-(N-pyrrolidinyl)ethoxy)-3-(2-(3-furyl)vinyl)-spiro[5.5]-undecane as a yellow oil. (E/Z stereoisomeric ratio: 50/50, determined by $^1$H-NMR-spectroscopy). TLC: Rf=0.29 ($SiO_2$ plates, chloroform/methanol 90/10). $^1$H-NMR (300 MHz, $CDCl_3$, ppm from TMS): 7.37 (2H, m), 7.31 (2H, m), 6.48 (1H, m), 6.42 (1H, m), 6.20–5.83 (2H, dd), 6.07–5.40 (2H, dd), 3.58 (2H, m), 3.22 (2H, m), 2.66 (4H, t), 2.55 (8H, m), 2.49 (1H, m), 2.01 (1H, m), 1.95–0.95 (32H, m).

A solution of 0.80 g of said oil in anhydrous diethylether was treated with 0.21 g of oxalic acid to give 0.65 g of (EZ)-9-(2-(N-pyrrolidinyl)ethoxy)-3-(2-(3-furyl)vinyl)-spiro[5.5]-undecane oxalate as a light yellow solid mp 118°–122° C.

EXAMPLE 2

(EZ)-9-(2-(N-Pyrrolidinyl)ethoxy)-3-(2-(2-oxo-[5H]-4-furyl)vinyl)-spiro[5.5]undecane I-b A solution 15.0 g of 4-bromomethyl-2-oxo-[5H]-furan (Martin R. et al., Helv.Chim. Acta, 1976, 59, 2724) in 100 ml of trimethylphosphite was refluxed for 2 hrs, while a stream of nitrogen was bubbled vigorously into the solution. The mixture was then evaporated to dryness and the residue was purified by chromatography (SiO$_2$; ethyl acetate/diethylether 50/50) to give 16.0 g of dimethyl (2-oxo-[5H]-4-furyl)methyl-phosphonate.

Sodium hydride (0.045 mg, 60% dispersion in mineral oil) was added under nitrogen atmosphere and at room temperature, to a mixture of 0.740 g of dimethyl (2-oxo-[5H]-4-furyl)methylphosphonate and 0.080 g of 9-(2-(N-pyrrolidinyl)ethoxy)-3-formyl-spiro[5.5]-undecane (I-af, Ex. 30) in 5 ml of anhydrous tetrahydrofuran. After 2 hrs the reaction was quenched with sodium dihydrogenophosphate (5% water solution) and diluted with ethyl acetate; the organic layer was separated, dried over sodium sulfate and evaporated to dryness under reduced pressure The residue was purified by flash chromatography (SiO$_2$; chloroform/methanol 80/20) to give 0.110 g of (EZ)-9-(2-(N-pyrrolidinyl)ethoxy)-3-(2-(2-oxo-[5H]-4-furyl)vinyl)-spiro[5.5]-undecane (I-b) as amorphous solid. TLC: Rf=0.32 (SiO$_2$ plates, chloroform/methanol 80/20). $^1$H-NMR (300 MHz, CDCl$_3$, ppm from TMS): 6.50–5.70 (2H, m); 6.30 (1H, bs); 4.81 (2H, bs); 3.68 (2H, t), 3.45(1H, m), 2.75 (2H, t), 2.70–2.00 (5H, m); 1.97–0.99 (22H, m).

EXAMPLE 3

(E)-9-(2-(N-Pyrrolidinyl)ethoxy)-3-(2-(3-pyridyl)-vinyl)-spiro-[5.5]undecane I-c
(Z)-9-(2-(N-Pyrrolidinyl)ethoxy)-3-(2-(3-pyridyl)-vinyl)-spiro[5.5]undecane I-d Using the same reaction conditions described in Ex. 1, and starting from pure (Z)-9-hydroxy-3-(2-(3-pyridyl)vinyl)spiro[5.5]undecane (I-aj, Ex. 33) and (E)-9-hydroxy-3-(2-(3-pyridyl)vinyl)spiro[5.5]-undecane (I-ak, Ex. 33), the title compounds (Ic and Id) were obtained. (E)-derivative (I-c): white amorphous solid TLC: Rf=0.35 (SiO$_2$ plates, chloroform/methanol 85/15). $^1$H-NMR (300 MHz, CDCl$_3$, ppm from TMS): 8.55 (1H, m), 8.47 (1H, m), 7.52 (1H, m), 7.27 (1H, m), 6.28–5.65 (2H, m), 3.68–3.60 (3H, m), 2.75 (2H, t), 2.70–2.45 (4H, m), 1.92–1.10 (21H, m). (Z)-derivative (I-d): amorphous solid TLC: Rf=0.35 (SiO$_2$ plates, chloroform/methanol 85/15). $^1$H-NMR (300 MHz, CDCl$_3$, ppm from TMS): 8.59 (1H, m), 8.42 (1H, m), 7.55 (1H, m), 7.27 (1H, m), 6.30–5.65 (2H, m), 3.70–3.65 (3H, m), 2.80 (2H, t), 2.70–2.50 (4H, m), 1.92–1.10 (21H, m)

EXAMPLE 4

(EZ)-9-(2-(N-Pyrrolidinyl)ethoxy)methyl-3-(3-furyl)-methyliden-spiro[5.5]undecane I-e Using, the same reaction conditions described in Ex. 1, and (EZ)-9-hydroxymethyl-3-(3-furyl)methyliden-spiro[5.5]undecane (I-al, Ex. 34) as starting material, the title compound (I-e) was obtained as a pasty solid: TLC: Rf=0.38 (SiO$_2$ plates, chloroform/methanol 95/05). $^1$H-NMR (300 MHz, CDCl$_3$, ppm from TMS): 7.38 (1H, m), 6.38 (1H, m), 5.89 (1H, m), 3.65 (2H, t), 3.50 (2H, d), 2.70–2.50 (4H, m), 2.45–2.15 (4H, m), 1.80–0.80 (17H, m).

EXAMPLE 5

(EZ)-9-(2-(N-Pyrrolidinyl)ethoxy)methyl-3-(2-oxo[5H]-4-furyl))methyliden-spiro[5.5]undecane I-f Using the same reaction conditions described in Ex. 2 and 9-(2-(N-pyrrolidinyl)ethoxy)methyl-3-oxo-spiro[5.5]undecane (II-c, Prep. 3) and dimethyl (2-oxo-[5H]-4-furyl)methylphosphonate as starting materials, the title compound (I-f) was obtained as a thick oil. TLC: Rf=0.29 (SiO$_2$ plates, chloroform/methanol 90/10). $^1$H-NMR (300 MHz, CDCl$_3$, ppm from TMS): 6.32 (1H, bs), 5.85 (1H, m), 4.80 (2H, bs), 3.58 (2H, t), 3.42 (2H, d), 2.75–2.50 (6H, m), 2.45–2.15 (4H, m), 1.80–0.80 (13H, m).

EXAMPLE 6

9-(2-(N-Pyrrolidinyl)ethoxy)-3-(2-(3-furyl)ethyl)-spiro[5.5]undecane I-g

Using the same reaction conditions described in Ex. 1 and 9-hydroxy-3-(2-(3-furyl)ethyl)-spiro[5.5]undecane (I-ap, Ex. 38) as starting material, the title compound (I-g) was obtained as a yellow gummy oil. $^1$H-NMR (300 MHz, CDCl$_3$, ppm from TMS): 7.35 (1H, m), 7.18 (1H, m), 6.25 (1H, m), 3.60 (2H, t), 3.21 (1H, hept), 2.67 (2H, t), 2.57 (4H, m), 2.43 (2H, t), 1.90–0.80 (23H, m).

A solution of 0.510 g of said oil in anhydrous diethylether was treated with 0.130 g of oxalic-acid to give 0.450 g of 9-(2-(N-pyrrolidinyl)ethoxy)-3-(2-(3-furyl)ethyl)-spiro[5.5]undecane oxalate, as a white solid mp 132°–134° C.

EXAMPLE 7

9-(2-(N-Pyrrolidinyl)ethoxy)-3-(2-(3-pyridyl)ethyl)-spiro[5.5]undecane I-h

Using the same reaction conditions described in Ex. 1 and 9-hydroxy-3-(2-(3-pyridyl)ethyl)-spiro[5.5]undecane (I-as, Ex. 40) as starting material, the title compound (I-h) was obtained as an amorphous solid. TLC: Rf=0.33 (SiO$_2$ plates, chloroform/methanol 90/10). $^1$H-NMR (300 MHz, CDCl$_3$, ppm from TMS): 8.40 (2H, m), 7.45 (1H, m), 7.15–7.10 (1H, m), 3.70 (2H, t), 3.30–3.20 (1H, m), 2.95–2.87 (6H, m), 2.58 (2H, dd), 1.95–1.85 (4H, m), 1.82–0.85 (19H, m).

EXAMPLE 8

(RS)-9-(2-(N-Pyrrolidinyl)ethoxy)-3-(2-(3-(RS)-tetrahydrofuryl)ethyl)-spiro[5.5]undecane I-i Using the same reaction conditions described in Ex. 1 and 9-hydroxy-3-(2-(3-tetrahydrofuryl)ethyl)-spiro[5.5]undecane (I-at, Ex. 41) as starting material, the title compound (I-i) was obtained as a transparent oil.

This base dissolved in diethylether and treated with gaseous hydrogen chloride, gives (RS)-9-(2-(N-pyrrolidinyl)ethoxy)-3-(2-(3-(RS)-tetrahydro-furyl)ethyl)-spiro[5.5]undecane hydrochloride, mp 137°–139° C. TLC: Rf=0.36 (SiO$_2$ plates, chloroform/methanol 90/10).

1H-NMR (300 MHz, CDCl$_3$, ppm from TMS): 4.00–3.60 (6H, m), 3.40–3.10 (2H, m), 2.40–1.90 (6H, m), 1.90–0.85 (28H, m).

EXAMPLE 9

9-(2-(N-Pyrrolidinyl)ethoxy)methyl-3-(3-furyl)methyl-spiro[5.5]undecane I-j

Using the same reaction conditions described in Ex. 1 and 9-hydroxymethyl-3-(3-furyl)methyl-spiro[5.5]undecane (I-au, Ex. 42) as starting material, the title compound (I-j) was obtained as a glassy yellow solid. TLC:

Rf=0.35 (SiO$_2$ plates, chloroform/methanol 95/05). $^1$H-NMR (300 MHz, CDCl$_3$, ppm from TMS): 7.35 (1H, m), 7.20 (1H, m), 6.23 (1H, m), 3.62 (2H, t), 3.47 (2H, d), 2.75 (2H, t), 2.70–2.40 (4H, m), 2.28 (2H, d), 1.91 (2H, dr), 1.60–0.80 (18H, m).

EXAMPLE 10

9-(2-(N-Pyrrolidinyl)ethoxy)methyl-3-(2-oxo-[5H]-4-furyl))methyl-spiro5.5]undecane I-k A suspension of 0.100 g of (EZ)-9-(2-(N-pyrrolidinyl)ethoxymeth-yl)-3-(2-oxo-[5H]-4-furyl))methyliden-spiro[5.5]undecane (I-f, Ex. 5) in 10 ml of ethyl acetate and 0.020 g of palladium on carbon (5%) was hydrogenated at room temperature and atmospheric pressure for 2 hrs, the suspension was filtered and the filtrate evaporated to dryness under reduced pressure. The residue was purified by flash chromatography (SiO$_2$; chloroform/methanol 92/08) to give 0.030 g of the title compound (I-k) as white foam. TLC: Rf=0.30 (SiO$_2$ plates, chloroform/methanol 92/08). $^1$H-NMR (300 MHz, CDCl$_3$, ppm from TMS): 5.91 (1H, bs), 4.92 (2H, bs), 3.70 (2H, t), 3.40 (2H, d), 2.75 (2H, t), 2.65–2.40 (4H, m), 2.15–1.90 (2H, m); 2.00–1.10 (18H, m).

EXAMPLE 11

9.-(2-(N-pyrrolidinyl)ethoxy)methyl-3-(3-pyridyl)methyl-spiro[5.5]undecane I-I

Using the same reaction conditions described in Ex. 1 and 9-hydroxymethyl-3-(3-pyridyl)methyl-spiro[5.5]undecane (I-aw, Ex. 44) as starting material, the title compound (I-l) was obtained as a pasty solid. TLC: Rf=0.32 (SiO$_2$ plates, chloroform/methanol 90/10). $^1$H-NMR (300 MHz, CDCl$_3$, ppm from TMS): 8.65 (1H, m), 8.42 (1H, m), 7.75 (1H, m), 7.30 (1H, m), 3.68 (2H, t), 3.50 (2H, d), 2.65 (2H, m), 2.75–2.60 (4H, m), 2.25–1.80 (4H, m), 1.75–0.90 (20H, m).

EXAMPLE 12

9-(3-(N-Pyrrolidinyl)propoxy)-3-(2-C$_3$-furyl)ethyl)-spiro[5.5]undecane I-m

Using the experimental conditions described in Ex. 1 and N-(3-chloropropyl)-pyrrolidine and 9-hydroxy-3-(2-(3-furyl)ethyl)-spiro[5.5]undecane (I-ap, Ex. 38) as starting materials, the title compound (I-m) was obtained as a light yellow amorphous solid. TLC: Rf=0.31 (SiO$_2$ plates, chloroform/methanol 90/10). $^1$H-NMR (300 MHz, CDCl$_3$, ppm from TMS): 7.35 (1H, m), 7.20 (1H, m), 6.26 (1H, m), 3.50 (2H, t), 3.20 (1H, hept), 2.55 (6H, m), 2.42 (2H, t), 2.00–0.90 (23H, m).

EXAMPLE 13

9-(2-(N-Morpholinyl)ethoxy)-3-(2-(3-furyl)ethyl)-spiro[5.5]undecane I-n

Using the experimental conditions described in Ex. 1 and N-(3-chloropropyl)-morpholine and 9-hydroxy-3-(2-(3-furyl)ethyl)-spiro[5.5]undecane (I-ap, Ex. 38), as starting materials the title compound (I-n) was obtained as an amorphous solid. TLC: Rf=0.35 (SiO$_2$ plates, chloroform/methanol 95/05). $^1$H-NMR (300 MHz, CDCl$_3$, ppm from TMS): 7.37 (1H, m), 7.20 (1H, m), 6.25 (1H, m), 3.60 (4H, m), 3.48 (2H, t), 3.20 (1H, hept), 2.50 (2H, t), 2.40 (4H, m), 2.35 (2H, t), 2.00–0.90 (23H, m).

EXAMPLE 14

9-(2-(4-Methylpiperazin-1-yl)ethoxy)-3-(2-(3-furyl)ethyl)-spirol[5.5]undecane I-o Using the experimental conditions described in Ex. 1 and 1-(2-chloroethyl)-4-methylpiperazine and 9-hydroxy-3-(2-(3-furyl)-ethyl)-spiro[5.5]undecane (I-ap, Ex. 38) as starting materials, the title compound (I-o) was obtained as sticky oil. TLC: Rf=0.33 (SiO$_2$ plates, chloroform/methanol 85/15). $^1$H-NMR (300 MHz, CDCl$_3$, ppm from TMS): 7.37 (1H, m), 7.20 (1H, m), 6.28 (1H, m), 3.50 (2H, t), 3.20 (1H, hept), 2.85 (4H, m), 2.40 (2H, t), 2.35 (4H, m), 2.33 (2H, t), 2.25–1.00 (21H, m).

EXAMPLE 15

9.(2-Aminoethoxy)-3-(2-(3-furyl)ethyl)-spiro[5.5]undecane I-p

Using the experimental conditions described in Ex. 1 and 2-chloroethylamine and 9-hydroxy-3-(2-(3-furyl)ethyl)-spiro[5.5]undecane (I-ap, Ex. 38) as starting materials, the title compound (I-p) was obtained as a viscous oil. TLC: Rf=0.38 (SiO$_2$ plates, chloroform/methanol 85/15). $^1$H-NMR (300 MHz, CDCl$_3$, ppm from TMS): 7.38 (1H, m), 7.19 (1H, m), 6.30 (1H, m), 4.50–4.20 (2H, bs), 3.50 (2H, t), 3.20 (1H, hept), 2.85 (4H, m), 2.70 (2H, t), 2.45 (2H, t), 2.33 (2H, t), 2.05–1.00 (17H, m).

EXAMPLE 16

9-(3-Aminopropoxy)-3-(2-(3-furyl)ethyl)-spiro[5.5]undecane I-q

Using the experimental conditions described in Ex. 1 and 3-chloropropylamine and 9-hydroxy-3-(2-(3-furyl)ethyl)-spiro[5.5]-undecane (I-ap, Ex. 38) as starting materials, the title compound (I-q) was obtained as light yellow foam. TLC: Rf=0.27 (SiO$_2$ plates, chloroform-/methanol 90/10). $^1$H-NMR (300 MHz, CDCl$_3$, ppm from TMS): 7.35 (1H, m), 7.20 (1H, m), 6.25 (1H, m), 4.50–4.20 (2H, bs), 3.50 (2H, t), 3.20 (1H, hept), 2.85 (4H, m), 2.70 (2H, t), 2.38 (2H, t), 2.33 (2H, t), 1.95–0.90 (19H, m).

EXAMPLE 17

9-(3-(N-Pyrrolidinyl)propoxy)methyl-3-(3-furyl)-methyl-spiro[5.5]undecane I-r

Using the experimental conditions described in Ex. 1 and 9-hydroxymethyl-3-(3-furyl)methyl-spiro[5.5]undecane (I-au, Ex. 42) and N-(3-chloropropyl)pyrrolidine as starting materials, the title compound (I-r) was obtained as a thick oil. TLC: Rf=0.22 (SiO$_2$ plates, chloroform/methanol 90/10). $^1$H-NMR (300 MHz, CDCl$_3$, ppm from TMS): 7.35 (1H, m), 7.20 (1H, m), 6.23 (1H, m), 3.65 (2H, t), 3.47 (2H, d), 2.76 (2H, t), 2.70–2.60 (4H, m), 2.28 (2H, d), 1.91 (2H, dt), 1.60–0.80 (20H, m)

EXAMPLE 18

9-(3-pyridylmethoxy)-3-(2-(3-furyl)ethyl)-spiro[5.5]undecane I-s

Using the experimental conditions described in Ex. 1 and 3-chloromethylpyridine and 9-hydroxy-3-(2-(3-furyl)ethyl)-spiro[5.5]-undecane (I-ap, Ex. 38) as starting materials, the title compound (I-s) was obtained as a white solid, mp 50°–51° C. TLC: Rf=0.17 (SiO$_2$ plates, n-hexane/ethyl acetate 80/20). $^1$H-NMR (300 MHz, CDCl$_3$, ppm from TMS): 8.60 (1H, bs), 8.55–8.50 (1H, bs) 7.40 (1H, bs), 7.30 (1H, bs), 6.30 (1H, bs), 4.60 (2H, s), 3.45–3.40 (1H, hept), 2.50–2.40 (2H, t), 1.90–1.70 (3H, m), 1.60–0.90 (16H, m).

EXAMPLE 19

9-(3-(N-Pyrrolidinyl)-2-hydroxypropoxy)-3-(2-(3-furyl)ethyl)-spiro[5.5]undecane I-t A solution of 0.150 g of 9-(oxiranylmethoxy)-3-(2-(3-furyl)ethyl)-spiro[5.5]-undecane (prepared as intermediate in Ex. 21) in 0.3 ml of pyrrolidine was stirred, at room temperature under nitrogen atmosphere, for 72 hrs. The mixture was then diluted with cyclohexane and evaporated to dryness several times, under reduced pressure The residue was ground with diisopropyl ether to give the title compound (I-t) as a light brown solid, mp 85°–87° C. TLC: Rf=0.55 (SiO$_2$ plates, chloroform/methanol 90/10). $^1$H-NMR (300 MHz, CDCl$_3$, ppm from TMS): 7.35 (1H, s), 7.20 (1H, s), 6.25 (1H, s), 3.90–3.80 (1H, m), 3.50–3.40 (2H, d), 3.30–3.20 (1H, hept), 2.75–2.60 (2H, m), 2.60–2.30 (4H,m), 1.90–0.90 (25H, m).

EXAMPLE 20

9-(2-Amino-3-hydroxypropoxy)-3-(2-(3-furyl)ethyl)-spiro[5.5]undecane I-u

A solution of 0.12 g of 9-(oxiranylmethoxy)-3-(2-(3-furyl)ethyl)-spiro[5.5]-undecane (prepared as intermediate in Ex. 21), 0.130 g of sodium azide and 0.030 g of tetrabutylammonium hydrogen sulfate in 1.5 ml of water and 1.5 ml of benzene was vigorously stirred at reflux temperature for 48 hrs. The reaction mixture was then cooled to room temperature, diluted with ethyl acetate, the organic phase washed with water several times, dried on sodium sulfate and evaporated to dryness. The residue was purified by chromatography (SiO$_2$; n-hexane/diethylether 50/50), to give 0.110 g of 9-(2-azido-3-hydroxypropoxy)-3-(2-(3-furyl)ethyl)-spiro[5.5]-undecane as brown foam. [TLC: Rf=0.48 (SiO$_2$ plates, diethylether/n-hexane 70/30). $^1$H-NMR (300 MHz, CDCl$_3$, ppm from TMS): 7.35 (1H, m), 7.20 (1H, m), 6.23 (1H, m), 4.00–3.80 (1H, m), 3.55–3.20 (5H, m), 2.42 (2H, t), 1.90–0.80 (19H, m)].

A mixture of 0.100 g of said azido-derivative and 0.01 g of palladium on carbon (5%) in 3 ml of methanol was hydrogenated at room temperature and atmospheric pressure for 1 hr. The suspension was then filtered and the filtrate evaporated to dryness. The residue was purified by chromatography (SiO$_2$; chloroform/methanol 80/20) to give 0.070 g of title compound (I-u) as a dense oil. TLC: Rf=0.21 (SiO$_2$ plates, chloroform/methanol 90/10). $^1$H-NMR (300 MHz, CDCl$_3$, ppm from TMS): 7.37 (1H, m), 7.20 (1H, m), 6.27 (1H, m), 5.60–4.60 (2H, bs), 3.77 (2H, m), 3.55–3.40 (2H, m), 3.28 (1H, m), 2.42 (2H, t), 1.90–0.80 (19H, m)

EXAMPLE 21

9-(3-Methoxy-2-hydroxypropoxy)-3-(2-(3-furyl)ethyl)-spiro5.5]undecane I-v

A mixture of 0.700 g of 9-hydroxy-3-(2-(3-furyl)ethyl)-spiro[5.5]undecane (I-ap, Ex. 38), 2.10 ml of epichlorohydrin, 0.030 g of tetrabutylammonium bromide, 2.5 ml of NaOH (40% water solution) was vigorously stirred at room temperature for 24 hrs.

The mixture was then neutralized with 0.1N HCl and extracted with ethyl acetate. The organic layer was washed with brine, dried over anhydrous sodium sulfate and evaporated to dryness under reduced pressure. The residue (1.12 g) was purified by flash chromatography (SiO$_2$; n-hexane/diethylether 90/10) to give 0.810 g of 9-(oxiranylmethoxy)-3-(2-(3-furyl)ethyl)-spiro[5.5]-undecane compound as a light yellow oil. TLC: Rf=0.41 (SiO$_2$ plates, n-hexane/diethylether 70/30). $^1$H-NMR (300 MHz, CDCl$_3$, ppm from TMS): 7.37 (1H, m), 7.20 (1H, m), 6.28 (1H, m), 4.07–3.25 (5H, m), 3.16 (1H, m), 2.41 (2H, t), 1.90–0.90 (19H, m).

A solution of 0.100 g of 9-(oxiranylmethoxy)-3-(2-(3-furyl)ethyl)-spiro[5.5]-undecane, 0.80 ml of tetrabutylammonium hydroxide in 2 ml of methanol was vigorously stirred at 50° C. for 1 hr. The reaction mixture was then cooled to room temperature, diluted with ethyl acetate, the organic phase washed with water several times, dried on sodium sulfate and evaporated to dryness. The residue, purified by chromatography (SiO$_2$; n-hexane/diethylether 50/50), gives 0.080 g of title compound (I-v) as a light oil. TLC: Rf=0.28 (SiO$_2$ plates, n-hexane/diethylether 50/50). $^1$H-NMR (300 MHz, CDCl$_3$, ppm from TMS): 7.36 (1H, m), 7.20 (1H, m), 6.27 (1H, m), 4.05–3.30 (5H, m), 3.28 (3H, s), 3.22 (1H, m), 2.43 (2H, t), 1.90–0.85 (19H, m).

EXAMPLE 22

9-(2,3-Dihydroxypropoxy)-3-(2-(3-furyl)ethyl)-spiro[5.5]undecane I-w

Aqueous perchloric acid (0.3 ml of 25% water solution) was added to a solution of 0.100 g of 9-(oxiranylmethoxy)-3-(2-(3-furyl)ethyl)-spiro[5.5]-undecane (prepared as intermediate in Ex. 2 1) in 3 ml of tetrahydrofuran, at room temperature under nitrogen atmosphere. The mixture was stirred for 6 hrs, diluted with water and extracted with ethyl acetate; the organic layer was washed with water, dried over sodium sulfate and evaporated to dryness; the residue was purified by flash-chromatography (SiO$_2$; n-hexane/ethyl acetate 80/20) to give 0.030 g of the title compound (I-w) as a pale yellow amorphous solid. TLC: Rf=0.35 (SiO$_2$ plates, n-hexane/ethylacetate 80/20). $^1$H-NMR (300 MHz, CDCl$_3$, ppm from TMS): 7.36 (1H, m), 7.20 (1H, m), 6.27 (1H, m), 3.95–3.40 (5H, m), 3.25 (1H, m), 2.43 (2H, t), 1.90–0.85 (19H, m).

EXAMPLE 23

9.(2-(N-pyrrolidinyl)ethoxy)-3-(2-(3-furyl)ethyl)-3-hydroxy-spiro[5.5]undecane I-x A mixture of 44.0 mg of magnesium and 2.0 mg of iodine in 1 ml of anhydrous tetrahydrofuran was stirred overnight at room temperature under argon atmosphere, then a solution of 310 mg of 3-(2-bromoethyl)furan (Tanis S. P. & Herrinton P. M., J. Org. Chem., 1985, 50, 3998) in 1.5 ml of anhydrous tetrahydrofuran was added and the mixture was heated at 50° C. for 2 hrs. The yellow-green solution was cooled to room temperature and poured into a solution of 500 mg of 9-(2-(N-pyrrolidinyl)ethoxy)-3-oxo-spiro[5.5]undecane (II-b, Prep. 2) in 2 ml of anhydrous tetrahydrofuran. The mixture was stirred at room temperature under argon atmosphere for 18 hrs, then sodium hydrogen carbonate (5% water solution) and ethyl acetate were added. The organic phase was washed with sodium dihydrogen phosphate (5% water solution) to neutral pH, dried over sodium sulfate and evaporated in vacuum. The residue (490 mg) was purified by chromatography (SiO$_2$; chloroform/methanol 95/05) to give 68.0 mg of the title compound (I-x)as a light yellow solid, mp 75°–78° C. TLC: Rf=0.19 (SiO$_2$ plates, chloroform/methanol 90/10). $^1$H-NMR (300 MHz, CDCl$_3$, ppm from TMS): 7.40 (1H, bs), 7.30 (1H, bs), 6.30 (1H, bs), 3.90–3.80(2H, m), 3.40–3.30 (1H, hept), 3.00–2.60 (6H, m), 2.55–2.45 (2H, dd), 2.00–1.00 (18H, m).

EXAMPLE 24

9-(2-Aminoethylthio)-3-(2-(3-furyl)ethyl)-spiro[5.5]undecane I-z

A solution of 0.200 g of 9-hydroxy-3-(2-(3-furyl)ethyl)-spiro[5.5]-undecane (I-ap, Ex. 38) and 0.11 ml of thiolacetic acid in 9 ml of anhydrous tetrahydrofuran was added to a solution of 0.40 g of triphenylphosphine and 0.30 ml of diisopropyl azodicarboxylate in 1 ml of anhydrous tetrahydrofuran, and the mixture stirred at 0° C. under argon atmosphere for 2 hrs. Silica gel was then added, the mixture was evaporated to dryness and the residue purified by chromatography ($SiO_2$; n-hexane/diethylether 90/10) to give 0.120 g of 9-acetylthio-3-(2(3-furyl)ethyl)-spiro[5.5]undecane as a light oil. TLC: Rf=0.72 ($SiO_2$ plates, n-hexane/diethylether 90/10). $^1$H-NMR (300 MHz, $CDCl_3$, ppm from TMS): 7.40 (1H, m), 7.21 (1H, m), 6.25 (1H, m), 3.48 (1H, m), 2.48 (2H, t), 2.30 (3H, s), 1.90–0.85 (19H, m).

A solution of 0.100 g of 9-acetylthio-3-(2-(3-furyl)ethyl)-spiro[5.5]undecane in 5 ml of methanol/tetrahydrofuran 3/1, was saturated with hydrogen and successively with gaseous ammonia and kept on standing for 3 hrs at room temperature. The mixture was evaporated to dryness and purified by flash chromatography ($SiO_2$; n-hexane/diethylether 80/20) to give 0.080 g of 9-mercapto-3-(2-(3-furyl)ethyl)-spiro[5.5]undecane as a white sticky oil. TLC: Rf=0.38 ($SiO_2$ plates, n-hexane/diethylether 80/20). $^1$H-NMR (300 MHz, $CDCl_3$, ppm from TMS): 7.36 (1H, m), 7.20 (1H, m), 6.27 (1H, m), 2.90 (1H, m), 2.48 (2H, t), 1.90–0.85 (19H, m).

A mixture of 0.050 g of 9-mercapto-3-(2-(3-furyl)ethyl)-spiro[5.5]undecane, 0.020 g of 2-chloroethylamine hydrochloride and 0.0100 g of sodium hydride (60% dispersion in mineral oil) in 1 ml of dimethylformamide was stirred under nitrogen atmosphere at room temperature for 2.5 hrs. The reaction was then quenched with HCl 0.5N, and extracted with methylene chloride; the organic layer was washed with water, dried over sodium sulfate, filtered and evaporated to dryness under reduced pressure. The crude product was purified by chromatography ($SiO_2$; chloroform/methanol/90/10) to give 0.020 g of the title compound (I-z) as a light brown amorphous solid. TLC: Rf=0.21 ($SiO_2$ plates, chloroform/methanol/90/10). $^1$H-NMR (300 MHz, $CDCl_3$, ppm from TMS): 7.37 (1H, m), 7.24 (1H, m), 6.26 (1H, m), 4.4–4.2 (2H, bs), 2.85 (2H, t), 2.70 (1H, m), 2.48 (2H, t), 2.39 (2H, t), 1.90–0.85 (19H, m).

EXAMPLE 25

9-(2-Amino-2-carboxy-ethylthio)-3-(2-(3-furyl)ethyl)-spiro[5.5]undecane I-aa Using the experimental conditions described in Ex. 24 and 9-mercapto-3-(2-(3-furyl)ethyl)-spiro[5.5]undecane and 3-chloroalanine hydrochloride as starting materials, the title compound (I-aa) was obtained as an amorphous solid. TLC: Rf=0.28 ($SiO_2$ plates, n-butanol/acetic acid/water 40/10/50). $^1$H-NMR (300 MHz, $CDCl_3$, ppm from TMS): 7.37 (1H, m), 7.24 (1H, m), 6.26 (1H, m), 4.4–4.2 (3H, m), 3.48 (1H, m), 2.70 (1H, m), 2.45 (2H, t), 2.42 (2H, t), 1.90–0.85 (19H, m).

EXAMPLE 26

9-(2-(N-Pyrrolidinyl)ethoxy)methyl-3-(3-furyl)methyl-3-hydroxy-spiro[5.5]undecane I-ab Using the experimental conditions for the synthesis of oxirane from ketones, described in Prep. 7 and 9-tert-butyldimethyl silyloxymethyl-3-oxo-spiro[5.5]-undecane (II-f, Prep. 6) as starting material 9-tert-butyldimethylsilyloxymethyl-1-oxa-dispiro-[2.2.5.2]-tridecane was obtained as white amorphous solid. TLC: Rf=0.62 ($SiO_2$ plates, n-hexane/diethylether 60/40). $^1$H-NMR (300 MHz, $CDCl_3$, ppm from TMS): 3.42 (2H, d); 2.60 (2H, s), 1.70–1.05 (17H, m), 0.89 (9H, s), 0.03 (6H, s).

25.4 ml of n-buthyllithium (1.6M in hexane) were dropped at −78° C. into a solution of 6.00 g of 3-bromofurane in 40 ml of diethylether. The mixture was stirred for 40 minutes, then a solution of 3.30 g the above prepared epoxide in 30 ml of diethylether and a solution of 5.80 g of freshly distilled $BF_3.Et_2O$ in 30 ml diethylether were rapidly added. After 2 hrs at −78° C., the reaction was quenched with $NaH_2PO_4$ (5%) and washed with diethylether. The combined organic layers were dried and evaporated in vacuum. The residue was purified by flash chromatography ($SiO_2$, cyclohexane/ethyl acetate 95/5) to give 2.80 g of 9-tert-butyl-dimethylsilyloxymethyl-3-(3-furyl)methyl-3-hydroxy-spiro-[5.5]undecane. [TLC: Rf -0.30 ($SiO_2$ plates, cyclohexane/diethylether 80/20). $^1$H-NMR (300 MHz, $CDCl_3$, ppm from TMS): 7.40 (1H, s); 7.28 (1H, s); 6.64 (1H, s); 3.42 (2H, d); 2.58 (2H, s), 1.90–0.95 (17H, m), 0.90 (9H, s), 0.03 (6H, s)].

This intermadiate was deprotected with tetrabutylammonium fluoride (9,10 g, 28,5 mmol) in THF (50 ml), to give 1.80 g of 9-hydroxymethyl-3-(3-furyl)-methyl-3-hydroxy-spiro[5.5]undecane, as a white solid. [TLC: Rf=0.30 ($SiO_2$ plates, cyclohexane/ethyl acetate 50/50). $^1$H-NMR (300 MHz, $CDCl_3$, ppm from TMS): 7.40 (1H, s); 7.28 (1H, s); 6.64 (1H, s); 3.50 (2H, d); 2.58 (2H, s), 1.90–0.95 (17H, m)]. 1.70 g of said compound and 370 mg of NaH (60%, dispersion in mineral oil) were stirred at room temperature for 30 minutes, then 2.20 g of N-(2-chloroethyl)-pyrrolidine was added and the mixture heated at reflux temperature for 25 hrs. After usual workup, the residue was purified by chromatography ($SiO_2$; chloroform/methanol 95/05) to give 1.20 g of title compound (I-ab), mp 63°–65° C. TLC: Rf=0.34 ($SiO_2$ plates, chloroform/methanol 80/20).

$^1$H-NMR (300 MHz, $CDCl_3$, ppm from TMS): 7.40 (1H, bs), 7.30 (1H, bs), 6.30 (1H, bs), 3.60 (2H, t), 3.25 (2H, d), 2.70 (2H, t), 2.60–2.50 (4H, m), 1.90–1.70 (4H, m), 1.60–0.90 (17H, m).

EXAMPLE 27

9-(2-(N-Pyrrolidinyl)ethoxy)-3-(guanidinoimino)-methyl-spiro[5.-5]undecane I-ac A solution of 150 mg 9-(2-(N-pyrrolidinyl)ethoxy)-3-formyl-spiro[5.5]undecane (I-af, Ex. 30) and 360 mg aminoguanidine bicarbonate in methanol (10 ml) and 1 ml of HCl (3N) was stirred at room temperature for 30 minutes and then evaporated to dryness. The residue was purified by chromatography ($SiO_2$, chloroform/methanol/ammonium hydroxide 30% 80/20/0.5) to give 60 mg of title compound (I-ac) as a light yellow foam. TLC: Rf=0.36 ($SiO_2$ plates, chloroform/methanol/ammonium hydroxide 30% 80/20/0.5). $^1$H-NMR (300 MHz, MeOD, ppm from TMS): 7,46 (1H, s), 5,10 (4H, m) 3.60 (2H, t), 3.40 (1H, hept), 2.85 (2H, t), 2.60–2.50 (4H, m), 2.30 (1H, m), 1.80–1.0 (20H, m).

EXAMPLE 28

(EZ)-9-(2-(N-Pyrrolidinyl)ethoxy)-3-(2-oxo)propylidene-spiro[5.5]undecane I-ad n-Butyllithium (2.3 ml; 1.6M solution in hexane) was added to a suspension of 0.600 g of dimethyl acetylmethylphosphonate in 10 ml of anhydrous tetrahydrofuran, and the mixture was stirred at room temperature under argon atmosphere for 15 min, then 0.200 g of 9-(2-(N-pyrrolidinyl)ethoxy)-3-oxo-spiro[5.5]undecane (II-b, Prep. 2) dissolved in 2 ml of anhydrous tetrahydrofuran were added. After 6 hrs the reaction was quenched with 5% N H$_4$Cl solution. The mixture was extracted several times with dichloromethane, the combined organic layers were dried over anhydrous sodium sulfate and evaporated to dryness under reduced pressure. The crude residue was purified by chromatography (SiO$_2$; chloroform/methanol 90/10) to give 0.12 g of title compound (I-ad) as an amorphous solid. TLC: Rf=0.36 (SiO$_2$ plates, chloroform/methanol 80/20) $^1$H-NMR (300 MHz, CDCl$_3$, ppm from TMS): 5.00 (1H, m), 3.72 (2H, t), 3.38 (1H, hept), 3.20–3.00 (6H, m), 2.32 (2H, t), 2.10–1.00 (24H, m).

EXAMPLE 29

9-(2-(N-pyrrolidinyl)ethoxy)-3-(2-oxo)propyl-spiro[5.5]-undecane I-ae

A mixture of 0.200 g of 9-(2-(N-Pyrrolidinyl)ethoxy)-3-(2-oxo)-propylidene-spiro[5.5]undecane (I-ad) and 20.0 mg of Pd/C (5%) in 10 ml of EtOH was hydrogenated at room temperature and atmospheric pressure for 4 hrs, then it was filtered and evaporated to dryness to give, after purification by chromatography (SiO$_2$; chloroform/methanol 90/10), 0.16 g of title compound (I-ae) as an amorphous solid. TLC: Rf=0.42 (SiO$_2$ plates, chloroform/methanol 80/20) $^1$H-NMR (300 MHz, CDCl$_3$, ppm from TMS): 3.72 (2H, t), 3.38 (1H, hept), 3.20–3.00 (6H, m), 2.32 (2H, t), 2.10–1.00 (25H, m).

EXAMPLE 30

9-(2-(N-pyrrolidinyl)ethoxy)-3-formyl-spiro[5.5]undecane I-af

Using 9-hydroxy-3-formyl-spiro[5.5]undecane (I-bc, Ex. 50) as starting material and the procedure described in the Prep. 2, the title compound (I-af) was obtained as dense white oil. TLC: Rf=0.52 (SiO$_2$ plates, chloroform/methanol 80/20). $^1$H-NMR (300 MHz, CDCl$_3$, ppm from TMS): 9.65 (1H, s), 3.60 (2H, t), 3.40 (1H, hept), 2.85 (2H, t), 2.60–2.50 (4H, m), 2.30 (1H, m), 1.80–1.0 (20H, m).

EXAMPLE 31

(EZ) 9-Hydroxy-3-(2-(3-furyl)vinyl)-spiro[5.5]undecane I-ag

An ethanolic solution of sodium ethoxide (obtained from 0.794 g of sodium in 15 ml of absolute ethanol) was dropped into a suspension of 12.07 g of (3-furyl)methyltriphenylphosphonium chloride (Jurasek A. et al., Collect. Czech. Chem. Commun., 1985, 2077; CA 105 (15): 133675g) in 110 ml of absolute ethanol, at room temperature under nitrogen atmosphere. After one hr, 7.81 g. of 9-acetoxy-3-formyl-spiro[5.5]undecane (IV, Prep. 7) were poured in and the mixture was kept at room temperature for 3 hrs. The reaction was then quenched with sodium dihydrogenphosphate (5% water solution) and the mixture was evaporated under reduced pressure to small volume. The residue was dissolved in ethyl acetate (250 ml), washed with brine, dried over sodium sulfate and evaporated under reduced pressure. The residue was purified by flash chromatography (SiO$_2$; n-hexane/diethylether 75/25) to give 5.44 g of (Z,E) 9-hydroxy-3(2-(3-furyl)vinyl)-spiro[5.5]undecane as an amorphous white solid (E/Z ratio: 50/50, determinated by $^1$H-NMR-spectroscopy). TLC: Rf=0.48 (SiO$_2$ plates, diethylether). $^1$H-NMR (300 MHz, CDCl$_3$, ppm from TMS): 7.40 (2H, m), 7.35 (2H, m), 6.51 (1H, m), 6.47 (1H, m), 6.20–5.90 (2H, dd), 6.07–5.45 (2H, dd), 3.63 (2H, m), 2.49 (1H, m), 2.05 (1H, m), 1.95–0.95 (32H, m).

EXAMPLE 32

(EZ)-9-Hydroxy-3-(2-(2-Oxo-[5H]-3-furyl)vinyl)-spiro[5.5]undecane I-ah
(EZ)-9-Hydroxy-3-(2-(2-oxo-[5H]-4-furyl)vinyl)-spiro[5.5]undecane I-ai a) m-Chloroperbenzoic acid (6.97 g) was added to a mixture of 0.950 g of sodium acetate, 0.6 ml of glacial acetic acid and 2.65 g of (Z,E) 9-hydroxy-3-(2-(3-furyl)-vinyl)-spiro[5.5]undecane (I-ag, Ex. 31) in 55 ml of dichloromethane, at 0° C. under nitrogen atmosphere. The mixture was stirred at room temperature for 2 hrs, then 1.63 g of tetrabutylammonium bromide and 2.08 g of sodium borohydride were added and the reaction mixture was stirred at room temperature overnight. Glacial acetic acid (1.33 ml) was then added and the reaction mixture was evaporated to dryness under reduced pressure. The residue was dissolved in 20 ml of dichloromethane, 10 g of silica gel were added and the whole was evaporated under reduced pressure. The residue was purified by flash chromatography (SiO$_2$; dichloromethane/diethylether 80/20) to give 0.660 g of (EZ)-9-hydroxy-3-(2-(2-oxo-[5H]-3-furyl)vinyl)-spiro[5.5]undecane (I-ah) as an amorphous solid and 0.580 g of (EZ)-9-hydroxy-3-(2-(2-oxo-[5H]-4-furyl)-vinyl)-spiro[5.5]undecane (I-ai) a white amorphous solid. 3-furyl-derivative (I-ah): TLC: Rf=0.21 (SiO$_2$ plates, n-hexane/ethyl acetate 50/50). $^1$H-NMR (300 MHz, CDCl$_3$, ppm from TMS): 7.20(1H, t); 6.50–5.60 (2H, m); 4.75 (2H, bs); 3.62(1H, m); 2.30–2.00 (1H, m); 1.95–0.92 (16H, m). 4-furyl-derivative (I-ai): TLC: Rf=0.25 (SiO$_2$ plates, n-hexane/ethyl acetate 50/50). $^1$H-NMR (300 MHz, CDCl$_3$, ppm from TMS): 6.50–5.70 (2H, m); 6.30 (1H, bs); 4.81 (2H, bs); 3.65(1H, m); 2.20–2.00 (1H, m); 1.97–0.99 (16H, m).

b) Using the same reaction conditions described in Ex. 2 and 9-hydroxy-3-formyl-spiro[5.5]undecane (I-bc, Ex. 50) and dimethyl (2-oxo-[5H]-4-furyl)methylphosphonate (intermediate described in Ex. 2) as starting materials, the title compound (EZ)-9-hydroxy-3-(2-(2-oxo-[5H]-4-furyl)vinyl)-spiro-[5.5]undecane (I-ai) was obtained as an amorphous solid, identical to the one above described.

EXAMPLE 33

(E)-9-Hydroxy-3-(2-(3-pyridyl)vinyl)-spiro[5.5]undecane I-aj
(Z)-9-Hydroxy-3-(2-(3-pyridyl)vinyl)-spiro[5.5]undecane I-ak Butyllithium (0.92 ml; 1.6M solution in hexane) was added to a suspension of 0.217 g of (3-picolyl)triphenylphosphonium chloride hydrochloride monohydrate (Baker B. R. et al. J. Med. Chem. 1971, 14, 797) in 5 ml of anhydrous tetrahydrofuran, at 0° C. under nitrogen atmosphere. The yellow-orange mixture was stirred at room temperature for 0.5 hrs, then a solution of 0.05 g of 9-tert-butyldimethylsilyloxy-3-formyl-spiro[5.5]undecane (V, Prep. 8) in 1 ml of anhydrous tetrahydrofuran was added and the mixture was stirred at room temperature overnight. The reaction was quenched with a saturated aqueous solution of ammonium chloride. The layers were separated and the aqueous phase was extracted with dichloromethane. The combined organic layers were dried over sodium sulfate and evaporated under reduced pressure. The crude residue was purified by flash chromatography (SiO$_2$; n-hexane/diethylether 70/30) to give 0.020 g of (E)-9-tert-butyldimethylsilyloxy-3-(2-(3-pyridyl)vinyl)-spiro[5.5]undecane and 0.020 g of (Z)-9-tert-butyldimethylsilyloxy-3-(2-(3-pyridyl)vinyl)-spiro[5.5]undecane as white amorphous solids.

(E)-derivative: TLC: Rf=0.32 (SiO$_2$ plates, n-hexane/diethylether 70/30). $^1$H-NMR (300 MHz, CDCl$_3$, ppm from TMS): 8.59 (1H, m), 8.42 (1H, m), 7.55 (1H, m), 7.27 (1H, m), 6.30–5.65 (AB system Jab=16 Hz), 3.60 (1H, m), 2.12 (1H, m), 1.92–0.82 (25H, m), 0.08 (6H, s). (Z)-derivative: TLC: Rf=0.38 (SiO$_2$ plates, n-hexane/diethylether 70/30). $^1$H-NMR (300 MHz, CDCl$_3$, ppm from TMS): 8.55 (1H, m), 8.47 (1H, m), 7.52 (1H, m), 7.27 (1H, m), 6.28–5.65 (AB system Jab=11.5 Hz), 3.60 (1H, m), 2.48 (1H, m), 1.92–0.82 (25H, m), 0.08 (6H, s), The separated isomer were reacted with tetrabutylammonium fluoride in 1 ml of anhydrous tetrahydrofuran to give after usual workup the title compounds as amorphous solids.

(E)-derivative (I-aj): TLC: Rf=0.48 (SiO$_2$ plates, dichloromethane/methanol 90/10). $^1$H-NMR (300 MHz, CDCl$_3$, ppm from TMS): 8.59 (1H, m), 8.42 (1H, m), 7.55 (1H, m), 7.27 (1H, m), 6.30–5.65 (2H, m), 3.60 (1H, m), 2.12 (1H, m), 1.92–1.1 (16H, m). (Z)-derivative (I-ak): TLC: Rf=0.48 (SiO$_2$ plates, dichloromethane/methanol 90/10). $^1$H-NMR (300 MHz, CDCl$_3$, ppm from TMS): 8.55 (1H, m), 8.47 (1H, m), 7.52 (1H, m), 7.27 (1H, m), 6.28–5.65 (2H, m), 3.60 (1H, m), 2.48 (1H, m), 1.92–1.1 (16H, m).

EXAMPLE 34

(EZ)-9-Hydroxymethyl-3-(3-furyl)methyliden-spiro[5.5]undecane I-al

Using the condition described in the Ex. 31 and 9-tert-butyldimethylsilyloxymethyl-3-oxo-spiro[5.5]-undecane (II-f, Prep. 6) and (3-furyl)methyltriphenylphosphonium chloride as starting materials, (EZ)-9-tert-butyldimethylsilyloxymethyl-3-(3-furyl)-methyliden-spiro[5.5]undecane was obtained as a light yellow oil. TLC: Rf=0.42 (SiO$_2$ plates, n-hexane/ethyl acetate 50/50). $^1$H-NMR (300 MHz, CDCl$_3$, ppm from TMS): 7.38 (1H, m), 6.38 (1H, m), 5.89 (1H, m), 3.40 (2H, d), 2.45–2.15 (4H, m), 1.80–0.80 (22H, m), 0.06 (6H, s).

A solution of 1.20 g of 9-tert-butyldimethylsilyloxymethyl-3-(3-furyl)methyliden-spiro[5.5]-undecane and 10 ml of tetrabutylammonium fluoride (1.1M solution in tetrahydrofuran) in 15 ml of anhydrous tetrahydrofuran were stirred under argon atmosphere at room temperature for 1 hr. After evaporation of the solvent at reduced pressure, the residue was purified by flash chromatography (SiO$_2$; cyclohexane/ethyl acetate 80/20) to give 0.9 g of (EZ)-9-hydroxymethyl-3-(3-furyl)methyliden-spiro[5.5]undecane (I-al) as an amorphous solid. TLC: Rf=0.35 (SiO$_2$ plates, n-hexane/ethyl acetate 75/25). $^1$H-NMR (300 MHz, CDCl$_3$, ppm from TMS): 7.38 (1H, m), 6.38 (1H, m), 5.89 (1H, m), 3.49 (2H, d), 2.45–2.15 (4H, m), 1.80–0.80 (13H, m).

EXAMPLE 35

(EZ)-9-Hydroxymethyl-3-((2-oxo-[5H]-4-furyl))-methyliden-spiro[5.5]undecane I-am Using the condition described in Ex. 2 and 9-tert-butyl-dimethylsilyloxymethyl-3-oxo-spiro[5.5]-undecane (II-f, Prep. 6) and dimethyl (2-oxo-[5H]-4-furyl)methylphosphonate as starting materials, (EZ)-9-tert-butyldimethylsilyloxymethyl-3-((2-oxo-[5H]-4-furyl))methyliden-spiro[5.5]undecane was obtained as an amorphous solid. TLC: Rf=0.38 (SiO$_2$ plates, n-hexane/ethyl acetate 50/50). $^1$H-NMR (300 MHz, CDCl$_3$, ppm from TMS): 5.90 (1H, bs); 5.85 (1H, bs); 4.91 (2H, bs); 3.42 (2H, d); 2.50–2.20 (4H, m); 1.97–0.99 (13H, m), 0.89 (9H, s), 0.06 (6H, s).

The silyl-derivative was deprotected to the free hydroxy compound (EZ)-9-hydroxymethyl-3-((2-oxo-[5H]-4-furyl))methylidenspiro-[5.5]undecane (I-am) using the procedure described in the Ex. 34. TLC: Rf=0.27 (SiO$_2$ plates, n-hexane/ethyl acetate 70/30). $^1$H-NMR (300 MHz, CDCl$_3$, ppm from TMS): 5.90 (1H, bs); 5.85 (1H, bs); 4.91 (2H, bs); 3.48 (2H, d); 2.50–2.20 (4H, m); 1.97–0.99 (13H, m).

EXAMPLE 36

(EZ)-9-Hydroxymethyl-3-(3-pyridyl)methyliden-spiro[5.5]undecane I-an

Using the conditions described in Ex. 33 and 9-tert-butyldimethylsilyloxymethyl-3-oxo-spiro[5.5]-undecane (II-f, Prep. 6) and (3-picolyl)triphenylphosphonium chloride hydrochloride monohydrate as starting materials, the title compound (I-an) was obtained as a transparent oil. TLC: Rf=0.36 (SiO$_2$ plates, n-hexane/ethyl acetate 60/40). $^1$H-NMR (300 MHz, CDCl$_3$, ppm from TMS): 8.65 (1H, m), 8.42 (1H, m), 7.75 (1H, m), 7.27 (1H, m), 6.85 (1H, m), 3.50 (2H, d), 2.38–2.20 (4H, m), 1.92–1.1 (12H, m).

EXAMPLE 37

(EZ).9-Hydroxy-3-((2-oxo-[5H1,4-furyl))methyliden-spiro[5.5]undecane I-ao

Using dimethyl (2-oxo-[5H]-4-furyl)methylphosphonate and 9-hydroxy-3-oxo-spiro[5.5]undecane (II-a, Prep. 1) as starting materials and the procedure described in Ex. 2, the title compound (I-ao) was obtained as an amorphous solid. TLC: Rf=0.45 (SiO$_2$ plates, n-hexane/diethylether 50/50). $^1$H-NMR (300 MHz, CDCl$_3$, ppm from TMS): 5.91 (1H, bs); 5.84 (1H, bs); 4.92 (2H, bs); 3.68 (2H, d); 2.40–2.20 (4H, m); 2.00–1.10 (12H, m).

EXAMPLE 38

9-Hydroxy-3-(2-(3-furyl)ethyl)-spiro5.5]undecane I-an

A suspension of 2.65 g of (EZ) 9-hydroxy-3-(2-(3-furyl)vinyl)-spiro[5.5]undecane (I-ag, Ex. 31) in 50 ml of ethanol and 0.26 g of palladium on carbon (5%) was hydrogenated at room temperature and atmospheric pressure for 2 hrs, then was filtered and the filtrate evaporated to dryness to give 2.59 g of pure 9-hydroxy-3-(2-(3-furyl)ethyl)-spiro[5.5]undecane (I-ap, Ex. 38) as white solid, mp 66°–69° C. TLC: Rf=0.42 (SiO$_2$ plates, n-hexane/diethylether 60/40). $^1$H-NMR (300 MHz, CDCl$_3$, ppm from TMS):7.35 (1H, m), 7.20 (1H, m), 6.25 (1H, m), 3.63 (1H, hept), 2.49 (2H, t), 1.95–0.95 (19H, m).

EXAMPLE 39

9-Hydroxy-3-(2-(2-oxo-[5H]-3-furyl)ethyl)-spiro[5.5]undecane I-aq
9-Hydroxy-3-(2-(2-oxo-[5H]-4-furyl)ethyl)-spiro[5.5]undecane Iar Using 9-hydroxy-3-(2-(3-furyl)ethyl)-spiro[5.5]undecane (I-ap, Ex. 38) as starting material and the procedure described in the Ex. 32-a) the title compounds were obtained as white solids. 3-furyl-derivative (I-aq): mp 123°–124° C. TLC: Rf=0.24 (SiO$_2$ plates, hexane/ethyl acetate 50/50). $^1$H-NMR (300 MHz, CDCl$_3$, ppm from TMS): 7.10 (1H, dd), 4.80 (2H, dd), 3.65 (1H, hept), 2.30 (2H, t), 1.90–0.90 (19H, m). 4-furyl-derivative (I-ar): mp 116°–117° C. TLC: Rf=0.23 (SiO$_2$ plates, hexane/ethyl acetate 50/50). $^1$H-NMR (300 MHz, CDCl$_3$, ppm from TMS): 5.80 (1H, bs), 4.70 (2H, bs), 3.65 (1H, hept), 2.45 (2H, t), 1.90–0.90 (19H, m).

EXAMPLE 40

9-Hydroxy-3-(2-(3-pyridyl)ethyl)-spiro[5.5]undecane I-as

Using the crude mixture (EZ)-9-hydroxy-3-(2-(3-pyridyl)vinyl)-spiro[5.5]undecane (I-aj+I-ak, Ex. 33) as starting material and the procedure described in the Ex. 38, the title compound (I-as) was obtained as a white solid: mp 108°–110° C. TLC: Rf=0.58 (SiO$_2$ plates, dichloromethane/methanol 50/50). $^1$H-NMR (300 MHz, CDCl$_3$, ppm from TMS): 8.50–8.40 (2H, m), 7.60–7.40 (1H, m), 7.25–7.15 (1H, m), 3.60 (1H, hept), 2.60 (2H, t), 1.90–0.90 (19H, m).

EXAMPLE 41

(RS) 9-Hydroxy-3-(2-(3-(RS)-tetrahydrofuryl)ethyl)-spiro[5.5]undecane I-at

A suspension of 0.770g of 9-hydroxy-3-(2-(3-furyl)ethyl)-spiro[5.5]undecane (I-ap, Ex. 38) in 5 ml of glacial acetic acid and 0.080 g of palladium on carbon (5%) was hydrogenated at room temperature and atmospheric pressure for 2 hrs, then the suspension was diluted with diethylether, filtered and the filtrate was washed with KOH (20%) and brine. The organic layer was dried over anhydrous sodium sulfate and evaporated under reduced pressure to give 0.70 g of title compound (I-at) as an amorphous solid, mp 38°–43° C.

Title compound (I-at) was a mixture of diastereoisomers, not separable by chromatography. TLC: Rf=0.46 (SiO$_2$ plates, diethylether/n-hexane 80/20). $^1$H-NMR (300 MHz, CDCl$_3$, ppm from TMS): 3.95–3.68 (4H, m), 3.61 (1H, hept), 3.31 (1H, t), 2.21–1.97 (2H, m), 1.90–0.90 (21H, m).

EXAMPLE 42

9-Hydroxymethyl-3-(3-furyl)methyl-spiro5.5]undecane I-au

Using (EZ)-9-hydroxymethyl-3-(3-furyl)methyliden-spiro[5.5]undecane (I-al, Ex. 34) as starting material and the procedure described in the Ex. 38, the title compound 9-hydroxymethyl-3-(3-furyl)methyl-spiro[5.5]undecane (I-au) was obtained as light yellow solid, mp 47°–50° C. TLC: Rf=0.40 (SiO$_2$ plates, n-hexane/ethyl acetate 70/30). H-NMR (300 MHz, CDCl$_3$, ppm from TMS): 7.35 (1H, m), 7.20 (1H, m), 6.23 (1H, m), 3.47 (2H, d), 2.28 (2H, t), 1.91 (2H, dt), 1.60–0.80 (16H, m).

EXAMPLE 43

9-Hydroxymethyl-3-((2-oxo-[5H]-4-furyl))methyl-spiro[5.5]undecane I-av

Using the conditions described in the Ex. 38 and (EZ)-9-hydroxymethyl-3-((2-oxo-[5H]-4-furyl))methyliden-spiro[5.5]unde-cane (I-am, Ex. 35) as starting material, the title compound (I-av) was obtained as an amorphous white solid. TLC: Rf=0.37 (SiO$_2$ plates, n-hexane/diethylether 50/50). $^1$H-NMR (300 MHz, CDCl$_3$, ppm from TMS): 5.91 (1H, bs), 4.92 (2H, bs), 3.40 (2H, d), 2.15–1.90 (4H, m); 2.00–1.10 (16H, m).

EXAMPLE 44

9-Hydroxymethyl-3-(3-pyridyl)methyl-spiro[5.5]undecane I-aw

Using the conditions described in the Ex. 38 and (EZ)-9-hydroxymethyl-3-(3-pyridyl)methyliden-spiro[5.5]-undecane (I-an, Ex. 36) as starting material, the title compound (I-aw) was obtained as an amorphous white solid. TLC: Rf=0.13 (SiO$_2$ plates, n-hexane/ethyl acetate 50/50). $^1$H-NMR (300 MHz, CDCl$_3$, ppm from TMS): 8.65 (1H, m), 8.42 (1H, m), 7.75 (1H, m), 7.30 (1H, m), 3.50 (2H, d), 2.25–1.80 (4H, m), 1.75–0.9 (16H, m).

EXAMPLE 45

9-Hydroxy-3-[2-(3-furyl)-2-hydroxy]propyl-spiro[5.5]undecane Iax

9-Hydroxy-3-(2-oxo)propyl-spiro[5.5]-undecane was prepared from 9-hydroxy-3-oxo-spiro[5.5]-undecane (IIa, Prep. 1) according to the methodology described in the Ex. 28 and 29. n-Buthyllithium (1.9 ml, 1.6M in hexane) was dropped at −78° C. into a solution of 0.460 g of 3-bromofurane in 8 ml of diethylether. The mixture was stirred for 1 hour then a solution of 0.200 g of 9-hydroxy-3-(2-oxo)propyl-spiro[5.5]-undecane in 2 ml of diethylether was added. After 0.5 hrs at −78° C., the reaction was quenched with NaH$_2$PO$_4$ (5%) and washed with diethylether. The combined organic layers were dried and evaporated in vacuum. The residue was purified by flash chromatography (SiO$_2$, diethylether/ethyl acetate 70/30) to give 0,0800 g of title compound (I-ax) as a light oil. TLC: Rf=0.30 (SiO$_2$ plates, diethylether/ethyl acetate 70/30). $^1$H-NMR (300 MHz, CDCl$_3$, ppm from TMS): 7.35 (1H, m), 7.18 (1H, m), 6.25 (1H, m), 3.21 (1H, hept), 1.90–0.80 (22H, m).

EXAMPLE 46

9-Hydroxymethyl-3-guanidinoimino-spiro[5.5]undecane I-ay

Using the experimental conditions described in Ex. 27 and 9-tert-butyldimethylsilyloxymethyl-3-oxo-spiro[5.5]undecane (II-f, Prep. 6) and aminoguanidine bicarbonate as starting materials, the title compound hydrochloride (I-ay) was obtained as a white solid, mp 198°–203° C. TLC: Rf=0.18 (SiO$_2$ plates, chloroform/methanol/ammonium hydroxide 30% 80/20/1). $^1$H-NMR (300 MHz, MeOD, ppm from TMS): 5.00–4.80 (5H, m); 3.40 (2H, d); 2.50–2.30 (4H, dt); 1.80–1.10 (13H, m).

EXAMPLE 47

9-Hydroxy-3-guanidinoiminomethyl-spirol[5.5]undecane I-az

Using the experimental conditions described in Ex. 27 and 9-tert-butyldimethylsilyloxy-3-formyl-spiro[5.5]undecane (V, Prep. 8) and aminoguanidine bicarbonate as starting materials, 9-hydroxy-3-guanidinoiminomethyl-spiro[5.5]undecane hydrochloride (I-az) was obtained as a white solid, mp 202°–205° C. TLC: Rf=0.20 (SiO$_2$ plates, chloroform/methanol/ammonium hydroxide 30% 80/20/1). $^1$H-NMR (300 MHz, MeOD, ppm from TMS): 7.40 (1H, d); 5.00–4.80 (5H, m); 3.62 (1H, hept); 2.30–2.00 (1H, m); 2.00–1.05 (16H, m).

EXAMPLE 48

9-Hydroxy-3-[2-(2-imidazolin-2-yl)hydrazono]methyl-spiro[5.5]undecane I-ba

A mixture of 100 mg of 9-tert-butyldimethylsilyloxy-3-formyl-spiro[5.5]undecane (V, Prep. 8) and 60.0 mg of 2-hydrazino-2imidazoline hydrobromide in 6 ml of dioxane was stirred at room temperature for 48 hours. The solvent was evaporated, the residue dissolved in 4 ml of methanol and 0.5 ml of HBr, stirred at room temperature for 1 hour and evaporated to dryness under reduced pressure. The crude residue was purified by chromatography (SiO$_2$; chloroform/methanol 95/05) to give 80.0 mg of title compound hydrobromide (I-ba)as a yellow solid, mp 2°–123° C. TLC: Rf=0.40 (SiO$_2$ plates, chloroform/methanol/ammonium hydroxide 30% 80/20/5). $^1$H-NMR (300 MHz, MeOD, ppm from TMS): 7.40(1H, d); 5.00–4.80 (4H, m); 3,70 (4H, s); 3.55 (1H, m); 2.30–2.20 (1H, m); 2.00–1.05 (16H, m).

EXAMPLE 49

9-Hydroxy-3-(3-guanidinoimino)propyl-spiro[5.5]-undecane I-bb

Using the experimental conditions described in Ex. 27 and 9-hydroxy-3-(2-oxo)propyl-spiro[5.5]-undecane (prepared as interme-diate in Ex. 45) and aminoguanidine bicarbonate as starting materials, the title compound (I-bb) was obtained as a foam. TLC: Rf=0.32 (SiO$_2$ plates, chloroform/methanol 80/20). $^1$H-NMR (300 MHz, MeOD, ppm from TMS): 7.40(1H, d); 5.00–4.80 (4H, m); 3,60 (1H, m); 2.30–2.20 (2H, m); 2.00–1.05 (19H, m).

EXAMPLE 50

9-Hydroxy-3-formyl-spiro[5.5]undecane I-bc

Potassium tert-butylate (1.44 g) was added in small portions, at 0° C. under nitrogen atmosphere, to a solution of 1.40 g of tosylmethylisocyanide and 1.00 g of 3-hydroxy-9-oxo-spiro[5.5]undecane (II-a, Prep. 1) dissolved in 7 ml of anhydrous tetrahydrofuran and 0.53 ml of absolute ethanol. After 0.5 hrs at room temperature, the mixture was filtered on an alumina cake. The cake was washed with dichloromethane and the filtrates, dried over anhydrous sodium sulfate, were evaporated under reduced pressure to give 0.52 g of crude 9-hydroxy-3-cyano-spiro[5.5]undecane as a light oil. [TLC: Rf=0.52 (SiO$_2$ plates, diethylether). $^1$H-NMR (300 MHz, CDCl$_3$, ppm from TMS): 3.63 (1H, hept), 2.57 (1H, m), 1.90–1.05 (16H, m)].

The crude nitrile (0.50 g), dissolved in 8 ml. of anhydrous benzene, was reacted with 3.6 ml. of diisobutylaluminum hydride (20% in hexane) at room temperature overnight. The mixture was quenched with sodium dihydrogenphosphate and extracted with ethyl acetate. The residue was purified by flash chromatography (SiO$_2$, n-hexane/diethylether). to give 0.22 g of title compound (I-be) as a transparent oil. TLC: Rf=0.73 (SiO$_2$ plates, diethylether). $^1$H-NMR (300 MHz, CDCl$_3$, ppm from TMS): 9.65 (d, $^1$H), 3.65 (1H, hept), 2.22 (1H, m), 1.89–0.85 (16H, m).

EXAMPLE 51

9-Thiomethyl-3-(3-furyl)methyl-spiro[5.5]undecane I-bd

A mixture of triphenylphosphine (1 g) and DIAD (0.75 ml) in THF (1 ml), is stirred at 0° C. for 30 min., then a solution of 9-hydroxymethyl-3-(3-furyl)methyl-spiro[5.5]undecane (I-au, Example 42) (500 mg) and thiolacetic acid (technical grade, 0.27 ml) in THF (9 ml) is added and the mixture is stirred at room temperature for 1 h. Silica gel is added, the mixture evaporated to dryness and the residue purified by flash-chromatography (SiO$_2$; n-hexane/diethylether 95/5) to give 557 mg (92%) of acetylthiomethyl-3-furylmethyl-spiro[5.5]undecane as a light oil. TLC: Rf-0.48 (n-hexane/diethylether 80/20). $^1$H-NMR: 7.38 (1H, m), 7.20 (1H, m), 6.25 (1H, m), 2.82 (2H, d). 2.40–2.30 (5H, m), 2.00–1.80 (2H, m), 1.60–0.80 (16H, m)

LiA$^1$H$_4$ (66 mg) is added to a solution of 9-acetylthiomethyl-3-(3-furyl)methyl-spiro[5.5]-undecane (550 mg) in THF (15 ml) at 0° C. After 1 h the mixture is poured into 1N HCl/ice (50 ml) and extracted several times with ethyl acetate. The combined organic layers were dried over anhydrous sodium sulfate and evaporated in vacuum to give 360 mg (75%) of I-bd as a white sticky foam. TLC: Rf=0.75 (nohexane/diethylether 80/20). $^1$H-NMR: 7.38 (1H, m), 7.20 (1H, m), 6.25 (1H, m), 2.45 (2H, m). 2.30 (2H, d), 2.00–1.80 (2H, m), 1.60–0.80 (16H, m)

EXAMPLE 52

9-(2-Aminoethylthiomethyl)-3-(3-furyl)methyl-spiro[5.5]undecane (I-be)

A mixture of 9-thiomethyl-3-(3-furyl)methyl-spiro[5.5]undecane (I-bd) (100 mg), 2-chloroethylamine hydrochloride (125 mg) and NaH (60%, 88 mg) in DMF (4 ml) is stirred at room temperature for 2.5 h. The reaction is poured in NaH$_2$PO$_4$/ice (25 ml) extracted with AcOEt the organic layer washed with water, dried over anhydrous sodium sulfate, filtered and evaporated to dryness. The crude product is purified by chromatography (SiO$_2$; chloroform/methanol 90/10) to give 103 mg (89%) of I-be as a light yellow solid. TLC: Rf=0.32 (chloroform/methanol 90/10).

A solution of I-be (100 mg, 0.32 mmol) and oxalic acid (29 mg, 0.32 mmol) in EtOH (0.6 ml) is gently stirred overnight to give 120 mg of I-be oxalate mp 145°–148° C.

EXAMPLE 53

9-(2-(N-Pyrrolidinyl)ethyl-thiomethyl)-3-(3-furyl)methyl-spiro[5.5]undecane I-bf Title compound is prepared, in 88% yield, starting from I-bd using N-(2-chloroethyl)-pyrrolidine in the same reaction conditions described in Ex. 52 for I-be. TLC: Rf=0.32 (chloroform/methanol 90/10).

A solution of I-bf and oxalic acid in EtOH is gently stirred overnight to give I-bf oxalate mp 168°–172° C.

EXAMPLE 54

9-(2-(N-pyrrolidinyl)ethoxy)-3-(2-(2-oxo-[5H]-3-furyl)ethyl)-spiro[5.5]undecane I-bg
9-(2-(N-Pyrrolidinyl)ethoxy)-3-(2-(2-oxo-[5H]-4-furyl)ethyl)-spiro[5.5]undecane I-bh Using the same procedure described in Ex. 32a for preparation of derivatives I-ah and I-ai, a solution of 1.5 g of 9-(2-(N-pyrrolidinyl)ethoxy)-3-(2-(3-furyl)ethyl)-spiro[5.5]undecane (I-g, Ex. 6) was oxidized with mCPBA (55%, 4.2 g), then treated with NaBH$_4$ (790 mg) to give after usual workup and flash chromathography (SiO$_2$, chloroform/methanol 90/10) 220 mg of a mixture of the of I-bg and I-bh N-oxides.

To said mixture of N-oxides (220 mg), i-PrOH (0.26 ml) and molecular sieves (4 Å, 60 mg) in methylene chloride (8 ml), TPAP (10 mg) was added. The mixture was stirred for 2 h then filtered on a celite pad, the eluate evaporated to dryness and purified by flash chromathography (SiO$_2$; chloroform/methanol 90/10) to give mg 40 of a mixture I-bg and I-bh (50:50 determined by $^1$H-NMR). Said mixture was purified by preparative TLC (Merck, PSC-Fertigplatten, Kieselgel 60 F$_{254}$, layer thickness 2 mm; two runs with chloroform/methanol 95/5) to give 27 mg (0.4%) of I-bg and 24 mg (0.2%) of I-bh. TLC (I-bg): Rf=0.34 (chloroform/methanol 90/10). $^1$H-NMR (300 MHz, CDCl$_3$, ppm from TMS): 7.08 (1H, m), 4,78 (2H, m), 3.58 (2H, t), 3.20 (1H, hept), 2.70 (2H, t), 2.62 (4H, m), 2.28 (2H, m), 1.90–0.80 (23H, m). TLC (I-bh): Rf=0.33 (chloroform/methanol 90/10) $^1$H-NMR (300 MHz, CDCl$_3$, ppm from TMS): 5.80 (1H, m), 4,65 (2H, m), 3.60 (2H, t), 3.20 (1H, hept), 2.70 (2H, t), 2.60 (4H, m), 2.40 (2H, m), 1.90–0.80 (23H, m).

Preparation 1

9-Hydroxy-3-qxo-spiro[5.5]undecane II-a

Sodium borohydride (0.400 g) was added in portions to a solution of 10.0 g of 3,9-dioxo-spiro[5.5]undecane (III) (Rice L. M. et al., J.Org.Chem., 1967, 32, 1966) in 80 ml of ethanol, under nitrogen atmosphere, at room temperature. After 1.5 hrs, 10.0 ml. of 1N hydrochloric acid were added and the resulting mixture was evaporated under reduced pressure. The crude residue, dissolved in 150 ml. of ethyl acetate, was washed with water to neutrality. The organic layer, dried over anhydrous sodium sulfate, was evaporated to dryness under reduced pressure to give a mixture of starting material, 3,9-dihydroxy- and 9-hydroxy-3-oxo-spiro[5.5]undecane. The components of the mixture were separated by flash chromatography (SiO$_2$; ethyl acetate/n-hexane 70/30) and 2.80 g of 9-hydroxy-3-oxo-spiro[5.5]undecane were obtained as a white solid, mp 65°–67° C. TLC: Rf=0.32 (SiO$_2$ plates, diethylether) $^1$H-NMR (300 MHz, CDCl$_3$, ppm from TMS): 3.75 (1H, hept), 2.35 (4H, q), 1.25–1.95 (12H, m)

Preparation 2

9-(2-(N-pyrrolidinyl)ethoxy)-3-oxo-spiro[5.5]undecane II-b

A mixture of 2.00 g of 9-hydroxy-3-oxo-spiro[5.5]undecane (II-a, Prep. 1), 3 ml of ethylene glycol and 0.020 g of p-toluensulfonic acid in 100 ml of benzene was refluxed in a Dean-Stark apparatus, under nitrogen atmosphere, for 2 hrs. The reaction mixture was then cooled to room temperature, diluted with ethyl acetate, washed with disodium hydrogen phosphate (5% water solution), dried over anhydrous sodium sulfate and evaporated in vacuum. The residue (2.30 g), N-(2-chloroethyl)pyrrolidine (2.75 g) and sodium hydride (0.830 g; 60 dispersion in oil) in 20 ml of anhydrous tetrahydrofuran were stirred under argon atmosphere at reflux temperature for 2.5 hrs in a Dean-Stark apparatus, and part of the distilled solvent collected, to the point of making the reaction a pasty stirrable mixture. The mixture was cooled to room temperature, sodium dihydrogenphosphate (5% water solution) and ethyl acetate were added and the organic layer was separated and thoroughly extracted with 1N HCl. The collected aqueous layers were made basic with 5% sodium carbonate and extracted with ethyl acetate to give, after workup, 2.5 g of a brown-yellow oil which was purified by flash chromatography (SiO$_2$; chloroform/methanol 90/10) to give 1.80 g of pure title compound (II-b) as an amorphous white solid. TLC: Rf=0.28 (SiO$_2$ plates, chloroform/methanol 90/10). $^1$H-NMR (300 MHz, CDCl$_3$, ppm from TMS): 3.62 (2H, t), 3.30 (1H, hept), 2.78 (2H, t), 2.70–2.55 (4H, m), 2.40–2.30 (4H, dd), 1.90–1.2 (16H, m).

Preparation 3

9-(2-(N-Pyrrolidinyl)ethoxy)methyl-3-oxospiro[5.5]undecane II-c

Using 9-hydroxymethyl-3-oxo-spiro[5.5]undecane (II-d, Prep. 4) as starting material and the procedure described in Prep. 2, the title compound (II-c) was obtained as a white amorphous solid. TLC: Rf=0.36 (SiO$_2$ plates, chloroform/methanol 85/15). $^1$H-NMR (300 MHz, CDCl$_3$, ppm from TMS): 3.65 (2H, t), 3.47 (2H, d), 2.75 (2H, t), 2.70–2.50 (4H, m), 2.40–2.30 (4H, dd), 1.60–0.80 (13H, m).

Preparation 4

9-Hydroxymethyl-3-oxo-spiro[5.5]undecane II-d

Sodium borohydride (65.0 mg) was added to a solution of 0.320 g 9-hydroxy-3-formyl-spiro[5.5]undecane in 5 ml of ethanol, at 0° C. under argon atmosphere. After 30 minutes the mixture was quenched with 2 ml. of 0.1N hydrochloric acid and evaporated under reduced pressure; the crude residue was dissolved in 10 ml. of ethyl acetate, the organic layer washed with water was dried over anhydrous sodium sulfate and evaporated to dryness to give 0.300 g of 9-hydroxy-3-hydroxymethyl-spiro[5.5]undecane as a transparent oil. TLC: Rf=0.35 (SiO$_2$ plates, ethyl acetate/n-hexane 65/35). $^1$H-NMR (300 MHz, CDCl$_3$, ppm from TMS): 3.63 (1H, hept), 3.45 (2H, d), 2.05–0.95 (17H, m).

9-Hydroxy-3-hydroxymethyl-spiro[5.5]undecane (0.29 g) and ammonium cerium sulfate (0.830 g) were added to a suspension of sodium bromate (0.230 g ) in acetonitrile and water (9 ml; 70:30). The mixture was heated at 80 ° C. for 3 hrs, cooled to 0 ° C., and treated with sodium bicarbonate to neutral pH. After evaporation under reduced pressure to small volume and extraction with ethyl acetate, the organic layers were dried over anhydrous sodium sulfate and evaporated under reduced pressure to give 0.220 g of a crude residue, that was purified by flash-chromatography (SiO$_2$; ethyl acetate/n-hexane 60/40) to give 0.200 g of 9-hydroxymethyl-3-oxo-spiro[5.5]undecane (II-d) a light oil. TLC: Rf=0.35 (SiO$_2$ plates, ethyl acetate/n-hexane 60/40). $^1$H-NMR (300 MHz, CDCl$_3$, ppm from TMS): 3.50 (2H, d), 2.36 (2H, t), 2.28 (2H, t), 1.85–1.09 (13H, m).

Preparation 5

9-tert-Butyldimethylsilyloxy-3-oxo-spiro[5.5]undecane II-e tert-Butyldimethylsilylchloride (6.14 g) was added, at 0° C. and under nitrogen atmosphere, to a solution of 6.00 g of 3-hydroxy-9-oxo-spiro[5.5]undecane (II-a, Prep. 1) in 35 ml of anhydrous pyridine. After 40 hrs at 0° C., the reaction mixture was poured into sodium hydrogen carbonate (5% water solution) and ice. Ethyl acetate was added, the two layers were separated, the organic washed with brine, dried over sodium sulfate and evaporated under reduced pressure. The residue was purified by chromatography (SiO$_2$; n-hexane/diethylether 90/10) to give 8.10 g of pure 9-tert-butyltrimethylsilyloxy-3-oxo-spiro[5.5]undecane as a pale yellow oil. TLC: Rf=0.65 (SiO$_2$ plates, diethylether/n-hexane 50/50). $^1$H-NMR (300 MHz, CDCl$_3$, ppm from TMS): 3.63 (1H, hept), 2.35 (4H, q), 1.90–1.05 (16H, m), 0.89 (9H, s), 0.06 (6H, s).

Preparation 6

9-tert-Butyldimethylsilyloxymethyl-3-oxo-spiro[5.5]undecane II-f

Sodium borohydride (0.110 g) was added, at 0° C. and under nitrogen atmosphere, to a solution of 1.35 g of 9-acetoxy-3-formyl-spiro[5.5]undecane (IV) in 50 ml of methanol. After 2 hrs, 10 ml. of a saturated aqueous ammonium chloride solution were added and the resulting mixture evaporated under reduced pressure. The residue, dissolved in 150 ml. of ethyl acetate, was washed with water to neutral pH; the organic layer, dried over anhydrous sodium sulfate, was evaporated under reduced pressure to give 1.50 g of 9-hydroxymethyl-3-acetoxy-spiro[5.5]undecane used as such in the following step. TLC: Rf=0.35 (SiO$_2$ plates, diethylether/n-hexane 55/45). $^1$H-NMR (300 MHz, CDCl$_3$, ppm from TMS): 4.73 (1H, hept), 3.47 (2H, d), 2.03 (3H, s) 1.90–0.95 (17H, m).

The hydroxymethyl derivative (1.40 g), dissolved in anhydrous pyridine (6 ml), was reacted overnight, at 0° C. and under nitrogen atmosphere, with 1.20 g of tert-butyldimethylsilylchloride, to give after usual workup 1.85 g of 9-tert-butyldimethylsilyloxymethyl-3-acetoxyspiro[5.5]undecane, as a light yellow oil, used as such for the following step. TLC: Rf=0.45 (SiO$_2$ plates, n-hexane/ethyl acetate 95/05). $^1$H-NMR (300 MHz, CDCl$_3$, ppm from TMS): 4.72 (1H, hept), 3.42 (2H, d), 2.00 (3H, s), 1.88–0.95 (17H, m), 0.88 (9H, s), 0.02 (6H, s).

The silyloxyderivative (1.78 g) and 2.4 ml of 30% aqueous potassium carbonate in 50 ml of methanol were stirred overnight at room temperature under nitrogen atmosphere. The solution was then cooled to 0° C., carefully neutralized with 1N HCl, evaporated under reduced pressure to give, after usual workup, 1.62 g of 9-tert-butyldimethylsilyloxymethyl-3-hydroxy-spiro[5.5]undecane as a white amorphous solid. TLC: Rf=0.38 (SiO$_2$ plates, n-hexane/diethylether 50/50). $^1$H-NMR (300 MHz, CDCl$_3$, ppm from TMS): 3.62 (1H, hept), 3.40 (2H, d), 1.90–0.95 (17H, m), 0.90 (9H, s), 0.02 (6H, s).

To a vigorously stirred mixture of 1.60 g of 9-tert-butyldimethylsilyloxymethyl-3-hydroxy-spiro[5.5]undecane and 0.100 g of molecular sieves (4 A, podwer) in 50 ml of anhydrous dichloromethane, 0.900 g of N-methylmorpholine-N-oxide and 0.0900 g of tetrapropylammonium perruthenate were added at 0° C. under nitrogen atmosphere After 2 hrs, 5.00 g of silica gel were added to the reaction and the mixture was evaporated under reduced pressure. The residue was purified by flash chromatography (SiO$_2$; n-he-xane/ethyl acetate 92/08) to give 1.50 g of pure title compound (II-f) as an amorphous solid. TLC: Rf=0.35 (SiO$_2$ plates, n-hexane/ethyl acetate 92/08). $^1$H-NMR (300 MHz, CDCl$_3$, ppm from TMS): 3.43 (2H, d), 2.36 (2H, t), 2.28 (2H, t), 1.78–1.62 (8H, m), 1.57–1.42 (1H, m), 1.30–1.03 (4H, m), 0.90 (9H, s), 0.02 (6H, s).

Preparation 7

9-Acetoxy-3-formyl-spiro[5.5]undecane IV

Sodium hydride (4.02 g) was added in small portions, at room temperature and under argon atmosphere, to a suspension of 20.1 g of trimethylsulfoxonium iodide in 150 ml of anhydrous tetrahydrofuran, and the mixture was kept at reflux temperature for 5 hrs. The suspension was then cooled to room temperature and a solution of 8.33 g of 3-hydroxy-9-oxo-spiro[5.5]undecane (II-a, Prep. 1) in 50 ml. of anhydrous tetrahydrofuran was quickly added. After 0.5 hrs, the reaction was quenched with sodium dihydrogen phosphate (5% water solution) and the mixture was evaporated under reduced pressure to small volume. The crude residue was dissolved in ethyl acetate (250 ml) and washed with brine to give, after usual workup, 11.7 g of crude 9-hydroxy-1-oxa-dispiro[2.2.5.2]tridecane TLC: Rf=0.70 (SiO$_2$ plates, diethylether/ethyl acetate 80/20). $^1$H-NMR (300 MHz, CDCl$_3$, ppm from TMS): 3.65 (1H, hept), 2.60 (2H, d), 1.10–1.90 (16H, m)

The crude epoxide, dissolved-in 37 ml. of anhydrous pyridine and 8.62 ml. of acetic anhydride, was kept at room temperature overnight. The mixture was then poured onto ice and 1N sulfuric acid and extracted with ethyl acetate to give after usual workup 14.1 g of crude 9-acetoxy-1-oxa-dispiro[2.2.5.2]tridecane, used as such in the next reaction without further purification. TLC: Rf=0.85 (SiO$_2$ plates, diethylether). $^1$H-NMR (300 MHz, CDCl$_3$, ppm from TMS):4.75 (1H, hept), 2.61 (2H, s), 2.05 (3H, s), 1.20–1.83 (16H, m). Freshly distilled borontrifluoride-diethylether complex (5.23 ml) was added, at 0° C. and under nitrogen atmosphere, to 8.50 g of crude 9-acetoxy-1-oxa-dispiro[2.2.5.2]-tridecano in 70 ml of anhydrous benzene. After 20 minutes, disodium hydrogen phosphate (5% water solution) was added, the organic layer separated and dried over anhydrous sodium sulfate to give 8.10 g of crude 9-acetoxy-3-formyl-spiro[5.5]undecane. After purification by chromatography (SiO$_2$; diethylether/n-hexane 25/75), 5.10 g of pure title compound (IV) was obtained as amorphous solid. TLC: Rf=0.55 (SiO$_2$ plates, nohexane/diethylether 65/35). $^1$H-NMR (300 MHz, CDCl$_3$, ppm from TMS) 9.67 (1H, d), 4.73 (1H, hept), 2.22 (1H, m), 2.03 (3H, s), 1.10–1.85 (16H, m)

Preparation 8

9-tert-Butyldimethylsilyloxy-3-formyl-spiro[5.5]undecane V

Using in the conditions described in Prep. 6 9-tert-butyltrimethyl silyloxy-3-oxo-spiro[5.5]undecane (II-e, Prep. 5) as starting material the title compound (V) was obtained as white amorphous solid. TLC: Rf=0.38 (SiO$_2$ plates, n-hexane/ethyl acetate 95/05). $^1$H-NMR (300 MHz, CDCl$_3$, ppm from TMS): 3.58 (1H, hept), 2.18 (s, $^1$H), 1.90–1.05 (16H, m), 0.89 (9H, s), 0.03 (6H, s).

We claim:
1. 3,9-disubstituted-spiro[5.5]undecanes of formula (I):

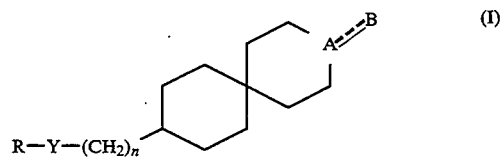

wherein:
R represents:
  hydrogen or
  a C$_2$–C$_6$ alkyl or C$_2$–C$_6$ alkenyl group unsubstituted or substituted independently by a quaternary ammonium group or one or more hydroxy, C$_1$–C$_6$ alkoxy, carboxy, NR$^4$R$^5$, NHC(NH)NHR$^6$ or C(NH)NR$^7$R$^8$ groups, wherein NR⁴R⁵ represents amino, methylamino, ethylamino, propylamino, isopropylamino, allylamino, propargylamino, dimethylamino, pyrrolidinyl, morpholino, piperazinyl, 4-methylpiperazinyl, 4-ethylpiperazinyl, 4-phenylpiperazinyl, 1-imidazolyl, guanidino, 2-aminoethylamino, 3-aminopropylamino, 2-(1-pyrrolidinyl)ethylamion, 3(1-pyrrolidinyl)propylamino, 3-amino-2-hydroxypropylamino, 3-(1-pyrrolidinyl)-2-hydroxypropylamino or 2,3-diaminopropylamino $R^6$, $R^7$ and $R^8$, which are the same or different, are H or $C_1$–$C_4$ lower alkyl;

n is an integer from 0 to 4; and

Y is oxygen or sulphur;

the symbol ≡≡≡ means single or double bond with the proviso that (i) when ≡≡≡ is a single bond A represents a C—H or C—OR¹ group wherein $R^1$ is H or $CH_3$ and B represents:

a $C_1$–$C_6$ lower alkyl or $C_2$–$C_6$ alkenyl chain substituted by hydroxy, amino, oxo, =N—NR²—C(=Z)NHR³; or a saturated or unsaturated mono-heterocyclic ring, wherein =N—NR²—C(=Z)NHR³ is guanidinoimino, ureidoimino, thioureidoimino, N-methylguanidimino, N,N'-dimethylguanidinoimino, (2-imidazolin-2-yl)hydrazono or 2-(2-imidazolyl)hydrazono, and, the saturated or unsaturated mono-heterocyclic ring is isoxyranyl, 2-aziridinyl, 2-furyl, 2-thienyl, 2-imidazolyl, 2-pirrolyl, 2-tetrahydrofuryl, 3-furyl, 3-thienyl, 4-imidazolyl, 3-pirrolyl, 3-tetrahydrofuryl, 2-oxo-(5H)-3-furyl, 2-oxo-(5H)-4-furyl, 2-thiazolyl, 2-pyridinyl, 3-pyridinyl, 4-pyridinyl, 2-pyrimidyl, 4-pyrimidyl, 5-pyrimidyl, 2-pyridinyl-N-oxide, 3-pyridinyl-N-oxide, 2-oxo-(1H)-4-pyridinyl, 2-oxo-(1H)-5-pyridinyl or 2-oxo-(2H)-5-pyranyl, and (ii) when ≡≡≡ is a double bond A represents a carbon atom C and B represents:

a =N—NR²—C(=Z)NHR³ group as above-identified;

and the pharmaceutically acceptable salts as well as the optical antipodes, i.e. the enantiomers, the racemic mixture of the optical antipodes, or other mixtures thereof, the geometric isomers and their mixtures, the diastereoisomers and mixtures of diastereoisomers of the compounds of formula (I).

2. A compound according to claim 1, which is selected from:

(EZ)-9-(2-(N-pyrrolidinyl)ethoxy)-3-(2-(3-furyl)vinyl)-spiro[5.5]undecane
9-(2-(N-pyrrolidinyl)ethoxy)-3-(2-(3-furyl)ethyl)-spiro[5.5]undecane
9-(2-(N-pyrrolidinyl)ethoxy)-3-(2-(3-thienyl)ethyl)-spiro[5.5]undecane
9-(2-(N-pyrrolidinyl)ethoxy)-3-(2-(2-oxo-[5H]-3furyl)ethyl)-spiro[5.5]undecane
9-(2-(N-pyrrolidinyl)ethoxy)-3-(2-(2-oxo-[5H]-4furyl)ethyl)-spiro[5.5]undecane
9-(2-(N-pyrrolidinyl)ethoxy)-3-(2-(3-pyridyl)ethyl)-spiro[5.5]undecane
9-(2-(N-pyrrolidinyl)ethoxy)-3-(2-(3-pyridyl-N-oxide)ethyl)-spiro[5.5]undecane
9-(2-(N-pyrrolidinyl)ethoxy)methyl-3-(3-furyl)methyl-spiro[5.5]undecane
9-(2-(N-pyrrolidinyl)ethoxy)methyl-3-(3-pyridyl)methyl-spiro[5.5]undecane
9-(2-(N-pyrrolidinyl)ethoxy)methyl-3-(2-thiazolyl)-methyl-spiro[5.5]undecane
9-(2-(N-pyrrolidinyl)ethoxy)methyl-3-(2-oxo-(2H)-5-pyranyl)methyl-spiro[5.5]undecane
9-(3-(N-pyrrolidinyl)propoxy)-3-(2-(3-furyl)ethyl)-spiro[5.5]undecane
9-(2-(4-methylpiperazin-1-yl)ethoxy)-3-(2-(3-furyl)ethyl)-spiro[5.5]undecane
9-(2-aminoethoxy)-3-(2-(3-furyl)ethyl)-spiro[5.5]undecane
9-(3-aminopropoxy)-3-(2-(3-furyl)ethyl)spiro[5.5]undecane
9-(3-aminopropoxy)-3-(2-(3-thienyl)ethyl)spiro[5.5]undecane
9-(3-(N-pyrrolidinyl)propoxy)methyl-3-(3-furyl)methyl-spiro[5.5]undecane
(EZ)-9-(2-(N-pyrrolidinyl)ethoxy)methyl-3-(3-furyl)-methyliden-spiro[5.5]undecane
(EZ)-9-(2-(N-pyrrolidinyl)ethoxy)methyl-3-(2-(2-oxo-[5H]-4-furyl))methyliden-spiro[5.5]undecane
9-(2-aminoethoxy)methyl-3-(3-furyl)methyl-spiro[5.5]undecane
9-(3-aminopropoxy)methyl-3-(3-furyl)methyl-spiro[5.5]undecane
9-(2-amino-3-hydroxypropoxy)-3-(2-(3-furyl)ethyl)-spiro[5.5]undecane
9-(3-amino-2-hydroxypropoxy)-3-(2-(3-furyl)ethyl)-spiro[5.5]undecane
9-(3-methoxy-2-hydroxypropoxy)-3-(2-(3-furyl)ethyl)-spiro[5.5]undecane
9-(2,3-dihydroxypropoxy)-3-(2-(3-furyl)ethyl)spiro[5.5]undecane
9-(2-(N-pyrrolidinyl)ethoxy)-3-(2-(3-furyl)ethyl)-3-hydroxy-spiro[5.5]undecane
9-(2-(N-pyrrolidinyl)ethoxy)-3-(2-(3-furyl)ethyl)-3-aminospiro[5.5]undecane
9-(2-aminoethylthio)-3-(2-(3-thienyl)ethyl)spiro[5.5]undecane
9-(2-aminoethylthio)methyl-3-(3-furyl)methylspiro[5.5]undecane
9-(2-aminoethylthio)methyl-3-(3-thienyl)methyl-spiro[5.5]undecane
9-(2-(N-pyrrolidinyl)ethylthio)-3-(2-(3-furyl)ethyl)-3-hydroxy-spiro[5.5]undecane
9-(2-(N-pyrrolidinyl)ethoxy)methyl-3-(3-furyl)methyl-3hydroxy-spiro[5.5]undecane
9-(2-(N-pyrrolidinyl)ethylthio)methyl-3-(3- thienyl)methyl3-hydroxy-spiro[5.5]undecane
9-(2-(N-pyrrolidinyl)ethoxy)-3-guanidinoimino-spiro[5.5]undecane
9-(2-(N-pyrrolidinyl)ethoxy)-3-guanidinoiminomethyl-spiro[5.5]undecane
9-(2-(N-pyrrolidinyl)ethoxy)methyl-3-guanidinoiminomethyl-spiro[5.5]undecane
9-(2-(N-pyrrolidinyl)ethoxy)-3-[2-(imidazolin-2yl)hydrazono]methyl-spiro[5.5]undecane
9-(2-(N-pyrrolidinyl)ethoxy)-3-[2-(imidazol-2yl)hydrazono]methyl-spiro[5.5]undecane
(EZ)-9-hydroxy-3-(2-(3-furyl)vinyl)-spiro[5.5]undecane
(EZ)-9-hydroxy-3-(2-(3-thienyl)vinyl)-spiro[5.5]undecane (EZ)-9-hydroxy-3-(2-(2-oxo-[5H]-3-furyl)vinyl)-spiro[5.5]undecane
(EZ)-9-hydroxy-3-(2-(2-oxo-[5H]-4-furyl)vinyl)-spiro[5.5]undecane
(E)-9-hydroxy-3-(2-(3-pyridyl)vinyl)-spiro[5.5]undecane
(Z)-9-hydroxy-3-(2-(3-pyridyl)vinyl)-spiro[5.5]undecane
(EZ)-9-hydroxymethyl-3-(3-furyl)methylidenspiro[5.5]undecane
(EZ)-9-hydroxymethyl-3-((2-oxo-[5H]-3-furyl))methyliden-spiro[5.5]undecane
(EZ)-9-hydroxymethyl-3-((2-oxo-[5H]-4-furyl))methyliden-spiro[5.5]undecane
9-hydroxy-3-(2-(3-furyl)ethyl)-spiro[5.5]undecane
9-hydroxy-3-(2-(3-pyridyl)ethyl)-spiro[5.5]undecane
9-hydroxy-3-(2-(3-pyridyl-N-oxide )ethyl)spiro[5.5]undecane
9-hydroxymethyl-3-(3-furyl)methyl-spiro[5.5]undecane
9-hydroxymethyl-3-(3-pyridyl)methyl-spiro[5.5]undecane
9-hydroxymethyl-3-(3-furyl)methyl-3-hydroxy-spiro[5.5]undecane
9-hydroxy-3-guanidinoimino-spiro[5.5]undecane
9-hydroxy-3-[2-(2-imidazolin-2-yl)hydrazono]spiro[5.5]undecane
9-hydroxy-3-[2-(2-imidazolyl)hydrazono]spiro[5.5]undecane
9-hydroxy-3-guanidinoiminomethyl-spiro[5.5]undecane
9-hydroxy-3-ureidoiminomethyl-spiro[5.5]undecane
9-hydroxy-3-[2-(2-imidazolin-2-yl)hydrazono]methyl-spiro[5.5]undecane
9-hydroxy-3-[2-(2-imidazolyl)hydrazono]methyl-spiro[5.5]undecane
9-hydroxy-3-thioureidoiminoethyl-spiro[5.5]undecane
9-hydroxy-3-(2-guanidinoimino)ethyl-spiro[5.5]undecane
9-hydroxy-3-(1-guanidinoimino)ethyl-spiro[5.5]undecane
9-hydroxy-3-(3-guanidinoimino)propyl-spiro[5.5]undecane
9-hydroxymethyl-3-guanidinoimino-spiro[5.5]undecane
9-hydroxymethyl-3-[2-(2-imidazolin-2-yl)hydrazono]-spiro[5.5]undecane
9-hydroxymethyl-3-[2-(2-imidazolyl)hydrazono]-spiro[5.5]undecane
9-hydroxymethyl-3-guanidinoiminomethylspiro[5.5]undecane
9-hydroxy-3-hydroxy-3-guanidinoiminomethyl-spiro[5.5]undecane
9-hydroxymethyl-3-[2-(imidazolin-2-yl)hydrazono]-methyl-spiro[5.5]undecane
9-hydroxymethyl-3-[2-(2-imidazolyl)hydrazono]methyl-spiro[5.5]undecane
9-hydroxymethyl-3-hydroxy-3-guanidinoiminomethyl-spiro[5.5]undecane their pharmaceutically acceptable salts as well as the optical antipodes, (enantiomers), the racemic mixture of the optical antipodes, or other mixtures thereof, the geometric isomers and their mixtures, the diastereoisomers and mixtures of diastereoisomers.

3. A pharmaceutical composition containing a compound of formula (I) as defined in claim 1 or a pharmaceutically acceptable salt thereof and a pharmaceutically acceptable excipient.

4. An orally or parenterally administrable pharmaceutical composition for the treatment of cardiovascular disorders comprising an effective amount of a compound of formula (I) as defined in claim 1 or an equivalent amount of a pharmaceutically acceptable salt thereof and an excipient therefor.

5. The composition of claim 4 for the treatment of hypertension.

6. The composition of claim 4 for the treatment of cardiac failure.

* * * * *